US006780878B2

(12) United States Patent
Beight et al.

(10) Patent No.: US 6,780,878 B2
(45) Date of Patent: Aug. 24, 2004

(54) ANTITHROMBOTIC AMIDES

(75) Inventors: Douglas Wade Beight, Frankfort, IN (US); Trelia Joyce Craft, Indianapolis, IN (US); Jeffry Bernard Franciskovich, Zionsville, IN (US); Theodore Goodson, Jr., Indianapolis, IN (US); Steven Edward Hall, Chapel Hill, NC (US); David Kent Herron, Indianapolis, IN (US); Sajan Joseph, Indianapolis, IN (US); Valentine Joseph Klimkowski, Carmel, IN (US); Jeffrey Alan Kyle, Fishers, IN (US); John Joseph Masters, Fishers, IN (US); David Mendel, Indianapolis, IN (US); Guy Milot, Chapel Hill, NC (US); Marta Maria Piñeiro-Núñez, Brownsburg, IN (US); Jason Scott Sawyer, Indianapolis, IN (US); Robert Theodore Shuman, Sedona, AZ (US); Gerald Floyd Smith, Greenwood, IN (US); Anne Louise Tebbe, Hamburg (DE); Jennifer Marie Tinsley, Ypsilanti, MI (US); Leonard Crayton Weir, Westfield, IN (US); James Howard Wikel, Greenwood, IN (US); Michael Robert Wiley, Indianapolis, IN (US); Ying Kwong Yee, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/382,614

(22) Filed: Mar. 5, 2003

(65) Prior Publication Data

US 2003/0212069 A1 Nov. 13, 2003

Related U.S. Application Data

(62) Division of application No. 09/857,747, filed as application No. PCT/US99/29832 on Dec. 15, 1999, now Pat. No. 6,610,704.

(60) Provisional application No. 60/113,778, filed on Dec. 23, 1998.

(51) Int. Cl.$^7$ ...................... C07D 312/02; A61K 31/44
(52) U.S. Cl. ....................................... 514/318; 546/194
(58) Field of Search .......................... 514/318; 546/194

(56) References Cited

U.S. PATENT DOCUMENTS

| 6,140,351 A | 10/2000 | Arnaiz et al. |
| 6,380,221 B1 | 4/2002 | Arnaiz et al. |

FOREIGN PATENT DOCUMENTS

| WO | WO 96/12499 | 5/1996 |
| WO | WO 97/24118 | 7/1997 |
| WO | WO 99/00121 | 1/1999 |
| WO | WO 99/00126 | 1/1999 |
| WO | WO 99/00127 | 1/1999 |
| WO | WO 99/00128 | 1/1999 |
| WO | WO 99/32477 | 7/1999 |
| WO | WO 00/39092 | 7/2000 |
| WO | WO 00/39117 | 7/2000 |
| WO | WO 00/39118 | 7/2000 |

OTHER PUBLICATIONS

U.S. patent application Ser. No. 09/994,284, filed Dec. 1997.
U.S. patent application Ser. No. 09/187,459, filed Nov. 1998.
Vacca, Joseph P. (Annette M. Doherty Section Editor), Annual Reports in Medicinal Chemistry, (1998), 33, 81–90.
Chemical Abstracts, vol. 116, No. 12, Mar. 30, 1992 Columbus, Ohio, US; abstract No. 128388p, Chernobrovin, N.U., et, al.: "Arylamides of N–(p–2',4'—or –3',4'–dimethoxybenzyl) anthranilic acid" p. 834; col. 2; XP002134048 abstract & SU 1 156 362 A (Perm Pharmaceutical Institute) Jul. 30, 1991.

*Primary Examiner*—Joseph K. McKane
*Assistant Examiner*—Kamal Saeed
(74) *Attorney, Agent, or Firm*—Thomas E. Jackson

(57) ABSTRACT

This application relates to a compound of formula I (or a pharmaceutically acceptable salt thereof) as defined herein, pharmaceutical compositions thereof, and its use as an inhibitor of factor Xa, as well as a process for its preparation and intermediates therefor.

10 Claims, No Drawings

ANTITHROMBOTIC AMIDES

This application is a divisional of application Ser. No. 09/857,747, filed Jun. 8, 2001, now U.S. Pat. No. 6,610,704 B1, the national stage application of PCT/US99/29832, filed Dec. 15, 1999 and claims the benefit of U.S. Provisional Application No. 60/113,778, filed Dec. 23, 1998.

This invention relates to antithrombotic aromatic amides which demonstrate activity as inhibitors of factor Xa and, accordingly, which are useful anticoagulants in mammals. In particular it relates to aromatic amides having high anticoagulant activity, and antithrombotic activity. Thus, this invention relates to new amides which are inhibitors of factor Xa. Pharmaceutical compositions containing the amides as active ingredients, and the use of the amides as anticoagulants for prophylaxis and treatment of thromboembolic disorders such as venous thrombosis, pulmonary embolism, arterial thrombosis, in particular myocardial ischemia, myocardial infarction and cerebral thrombosis, general hypercoagulable states and local hypercoagulable states, such as following angioplasty and coronary bypass operations, and generalized tissue injury as it relates to the inflammatory process. In addition, the antithrombotic agents are useful as anticoagulants in in vitro applications.

The process of blood coagulation, thrombosis, is triggered by a complex proteolytic cascade leading to the formation of thrombin. Thrombin proteolytically removes activation peptides from the Aα-chains and the Bβ-chains of fibrinogen, which is soluble in blood plasma, initiating insoluble fibrin formation. The formation of thrombin from prothrombin is catalyzed by factor Xa.

Anticoagulation currently is achieved by the administration of heparins and coumarins. Parenteral pharmacological control of coagulation and thrombosis is based on inhibition of thrombin through the use of heparins. Heparins act indirectly on thrombin by accelerating the inhibitory effect of endogenous antithrombin III (the main physiological inhibitor of thrombin). Because antithrombin III levels vary in plasma and because clot-bound thrombin seems resistant to this indirect mechanism, heparins can be an ineffective treatment. Because coagulation assays are believed to be associated with efficacy and with safety, heparin levels must be monitored with coagulation assays (particularly the activated partial thromboplastin time (APTT) assay). Coumarins impede the generation of thrombin by blocking the posttranslational gamma-carboxylation in the synthesis of prothrombin and other proteins of this type. Because of their mechanism of action, the effect of coumarins can only develop slowly, 6–24 hours after administration. Further, they are not selective anticoagulants. Coumarins also require monitoring with coagulation assays (particularly the prothrombin time (PT) assay).

Recently, interest has grown in small synthetic molecules which demonstrate potent direct inhibition of thrombin and factor Xa. See, Joseph P. Vacca (Annette M. Doherty Section Editor), *Annual Reports in Medicinal Chemistry*, (1998), 33, 81–90.

Although the heparins and coumarins are effective anticoagulants, there still exists a need for anticoagulants which act selectively on factor Xa or thrombin, and which, independent of antithrombin III, exert inhibitory action shortly after administration, preferably by an oral route, and do not interfere with lysis of blood clots, as required to maintain hemostasis.

The present invention is directed to the discovery that the amides of the present invention, as defined below, are potent inhibitors of factor Xa which may have high bioavailability following oral administration.

According to the invention there is provided a compound of formula I

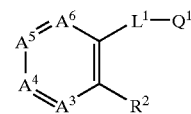

(or a pharmaceutically acceptable salt thereof) wherein:

$A^3, A^4, A^5$ and $A^6$, together with the two carbons to which they are attached, complete a substituted benzene in which $A^3$ is $CR^3$, $A^4$ is $CR^4$, $A^5$ is $CR^5$, and $A^6$ is $CR^6$; wherein $R^3$ is hydrogen;

one of $R^4$ and $R^5$ is hydrogen, methyl, fluoro, chloro, $R^fO_2C$—, or $R^gNH$—;

the other of $R^4$ and $R^5$ is hydrogen; and $R^6$ is hydrogen;

in which $R^f$ is hydrogen, (1–4C)alkyl or benzyl; $R^g$ is hydrogen, or $R^hSO_2$—; and $R^h$ is (1—4C)alkyl or dimethylamino; or $A^3, A^4, A^5$ and $A^6$, together with the two carbons to which they are attached, complete a substituted heteroaromatic ring in which (a) one of $A^3, A^4, A^5$ and $A^6$ is N, and each of the others is $CR^3, CR^4, CR^5$ or $CR^6$, respectively; or (b) two non-adjacent residues of $A^3, A^4, A^5$ and $A^6$ are each N, and each of the others is $CR^3, CR^4, CR^5$ or $CR^6$, respectively; wherein each of $R^3, R^4, R^5$ and $R^6$ is independently hydrogen or methyl, or one of $R^3, R^4, R^5$ and $R^6$ attached to a carbon which is not bonded to an N-atom is chloro and the others are hydrogen;

$L^1$ is —NH—CO—, —CO—NH— or —CH$_2$—NH— such that —$L^1$—$Q^1$ is —NH—CO—$Q^1$ —CO—NH—$Q^1$ or —CH$_2$—NH—$Q^1$;

$Q^1$ is phenyl, 2-furanyl, 2-thienyl, 4-thiazolyl, 2-pyridyl, 2-naphthyl, 1,2-dihydrobenzofuran-5-yl, 1,2-dihydrobenzofuran-6-yl, 1,2-benzisoxazol-6-yl, 6-indolyl, 6-indolinyl, 6-indazolyl, 5-benzimidazolyl or 5-benzotriazolyl in which the phenyl may bear one, two or three substituents at the 3-, 4- or 5-position(s) independently selected from halo, cyano, carbamoyl, aminomethyl, methyl, methoxy, difluoromethoxy, hydroxymethyl, formyl, vinyl, amino, hydroxy and 3,4-methylenedioxy; and in addition the phenyl may bear a 2-chloro or 2-fluoro substituent, the 2-furanyl or 2-thienyl may bear a chloro or methyl substituent at the 5-position; the 4-thiazolyl may bear an amino substituent at the 2-position; the 2-pyridyl may bear an amino substituent at the 6-position; the 1,2-benzisoxazol-6-yl, 6-indolyl or 6-indazolyl may bear a chloro or methyl substituent at the 3-position; or —CO—$Q^1$ is cyclopentenylcarbonyl or cyclohexenylcarbonyl;

$R^2$ is —NH—CH$_2$—$Q^2$ in which $Q^2$ is $Q^{2A}$ or $Q^{2B}$ wherein $Q^{2A}$ (showing the —CH$_2$— to which it is attached) is

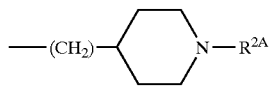

in which $R^{2A}$ is hydrogen, t-butyl, methylsulfonyl, —CHR$^y$R$^z$, —CHR$^w$R$^x$, or 4-pyridinyl (which is unsubstituted or bears a substituent R$^v$ at the 2- or 3-position) wherein R$^v$ is methyl, hydroxymethyl, {(1–2C)alkoxy}carbonyl; cyano, carbamoyl, thiocarbamoyl, or N-hydroxyamidino;

each of R$^w$ and R$^x$ independently is hydrogen or (1–3C) normal alkyl; or —CHR$^w$R$^x$ is 2-indanyl or (showing the nitrogen to which it is attached) is

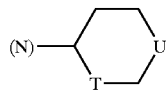

in which T is a single bond or methylene and U is methylene, ethylene, oxy, —S(O)$_q$— (wherein q is 0, 1 or 2) or imino (which may bear a methyl substituent), or T is ethan-1,1-diyl and U is a single bond or methylene;

R$^y$ is hydrogen or methyl; and

R$^z$ is isopropyl, t-butyl, (3–6C)cycloalkyl, phenyl (which is unsubstituted or bears one or more substituents independently selected from halo, methyl, methoxy and hydroxy), 4-quinolinyl or heteroaryl (which heteroaryl is a 5-membered aromatic ring which includes one to four heteroatoms selected from sulfur, oxygen and nitrogen or is a 6-membered aromatic ring which includes one to three nitrogen atoms, wherein the heteroaryl is attached at carbon and may bear one or more methyl substituents on carbon or nitrogen); and $Q^{2B}$ (showing the methylene to which it is attached) is

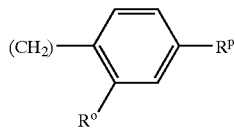

in which R$^o$ is hydrogen, halo, (1–6C)alkyl, hydroxy, (1–4C)alkoxy, benzyloxy or (1–4C)alkylthio; and R$^p$ is 4-morpholinyl, 1-hydroxyethyl, 1-hydroxy-1-methylethyl, 1-methoxy-1-methylethyl, 4-piperidinyl, 4-pyridinyl, dimethylaminosulfonyl or —J—R$^q$ in which J is a single bond, methylene, carbonyl, oxy, —S(O)$_q$ (wherein q is 0, 1 or 2), or —NR$^r$— (wherein R$^r$ is hydrogen or methyl); and R$^q$ is (1–6C)alkyl, phenyl, 3-pyridyl or 4-pyridyl.

As used herein, the expression a compound of formula I or the expression a compound of the invention includes the compound and any conventional prodrug thereof, as well as a pharmaceutically acceptable salt of said compound or prodrug.

A pharmaceutically acceptable salt of an antithrombotic agent of the instant invention includes one which is an acid-addition salt made from a basic compound of formula I and an acid which provides a pharmaceutically acceptable anion, as well as a salt which is made from an acidic compound of formula I and a base which provides a pharmaceutically acceptable cation. Thus, a salt of a novel compound of formula I as provided herein made with an acid or base which affords a pharmaceutically acceptable counterion provides a particular aspect of the invention. Examples of such acids and bases are provided hereinbelow.

As an additional aspect of the invention there is provided a pharmaceutical formulation comprising in association with a pharmaceutically acceptable carrier, diluent or excipient, a novel compound of formula I (or a pharmaceutically acceptable salt thereof) as provided in any of the descriptions herein.

In addition, there is provided the use of a factor Xa inhibiting compound of formula I (or prodrug or salt) as described herein as an active ingredient in the manufacture of a medicament for use in producing an anticoagulant or antithrombotic effect.

The present invention also provides a method of inhibiting coagulation in a mammal comprising administering to a mammal in need of treatment, a coagulation inhibiting dose of a factor Xa inhibiting compound of formula I having any of the definitions herein.

The present invention further provides a method of inhibiting factor Xa comprising administering to a mammal in need of treatment, a factor Xa inhibiting dose of a factor Xa inhibiting compound of formula I having any of the definitions herein.

Further, the present invention provides a method of treating a thromboembolic disorder comprising administering to a mammal in need of treatment, an effective dose of a factor Xa inhibiting compound of formula I having any of the definitions herein.

In addition, there is provided the use of a factor Xa inhibiting compound of formula I having any of the definitions herein for the manufacture of a medicament for treatment of a thromboembolic disorder.

As an additional feature of the invention there is provided a pharmaceutical formulation comprising in association with a pharmaceutically acceptable carrier, diluent or excipient, a prodrug of a factor Xa inhibiting compound of formula I (or of a pharmaceutically acceptable salt thereof) as provided in any of the descriptions herein.

In this specification, the following definitions are used, unless otherwise described: Halo is fluoro, chloro, bromo or iodo. Alkyl, alkoxy, etc. denote both straight and branched groups; but reference to an individual radical such as "propyl" embraces only the straight chain ("normal") radical, a branched chain isomer such as "isopropyl" being specifically denoted.

Particular values are listed below for radicals, substituents, and ranges, for illustration only, and they do not exclude other defined values or other values within defined ranges for the radicals and substituents.

For an alkyl group or the alkyl portion of an alkyl containing group such as, for example alkoxy, a particular value for (1–2C)alkyl is methyl or ethyl, and more particularly is methyl; for (1–3C)normal alkyl is methyl, ethyl or propyl; for (1–4C)alkyl is methyl, ethyl, propyl, isopropyl, butyl, isobutyl, or t-butyl, and more particularly is methyl, isopropyl, butyl or t-butyl; for (1–6C)alkyl is methyl, ethyl, propyl, butyl, pentyl or hexyl, and more particularly is methyl, butyl, or hexyl. A particular value for (3–6C)cycloalkyl is cyclopropyl, cyclobutyl, cyclopenytyl or cyclohexyl. A particular value for halo is bromo or chloro, and more particularly is chloro.

A particular value for $Q^1$ is 4-chlorophenyl, 4-methoxyphenyl, 3-fluoro-4-methoxyphenyl, 5-chlorothiophen-2-yl, 2-pyridinyl or 6-indolyl. A particular value for $R^2$ is 4-(4-morpholinyl)benzylamino, [1-(4-pyridinyl)piperin-4-yl-methyl]amino, or (1-isopropylpiperidin-4-yl-methyl)amino. When none of $A^3$–$A^6$ is N, a particular set of values for $R^3$–$R^6$ is that each of $R^3$–$R^6$ is hydrogen; and another particular set of values for $R^3$–$R^6$ is that each of $R^3$, $R^4$ and $R^6$ is hydrogen and $R^5$ is chloro. A further particular set of values is that $A^3$ is N and each of $A^4$–$A^6$ is CH.

A particular value for —$L^1$—$Q^1$ is —CO—NH—$Q^1$.

Particular species are those listed below in the examples, and more particularly examples 8, 9, 11, 12, 14 and 15.

It will be appreciated that certain compounds of formula I (or salts or prodrugs, etc.) may exist in, and be isolated in, isomeric forms, including tautomeric forms, cis- or trans-isomers, as well as optically active, racemic, or diastereomeric forms. It is to be understood that the present invention encompasses a compound of formula I in any of the tautomeric forms or as an a mixture thereof; or as a mixture of diastereomers, as well as in the form of an individual diastereomer, and that the present invention encompasses a compound of formula I as a mixture of enantiomers, as well as in the form of an individual enantiomer, any of which mixtures or form possesses inhibitory properties against factor Xa, it being well known in the art how to prepare or isolate particular forms and how to determine inhibitory properties against factor Xa by standard tests including those described below.

In addition, a compound of formula I (or salt or prodrug, etc.) may exhibit polymorphism or may form a solvate with water or an organic solvent. The present invention also encompasses any such polymorphic form, any solvate or any mixture thereof.

A prodrug of a compound of formula I may be one formed in a conventional manner with a functional group of the compound, such as with an amino, hydroxy or carboxy group.

A compound of formula I may be prepared by processes which include processes known in the chemical art for the production of structurally analogous compounds or by a novel process described herein. A process for the preparation of a compound of formula I (or a pharmaceutically acceptable salt thereof) and novel intermediates for the manufacture of a compound of formula I as defined above provide further features of the invention and are illustrated by the following procedures in which the meanings of the generic radicals are as defined above, unless otherwise specified. It will be recognized that it may be preferred or necessary to prepare a compound of formula I in which a functional group is protected using a conventional protecting group, then to remove the protecting group to provide the compound of formula I.

Thus, there is provided a process for preparing a compound of formula I (or a pharmaceutically acceptable salt thereof) as provided in any of the above descriptions which is selected from any of those described in the examples, including the following.

(A) For a compound of formula I in which —$L^1$—$Q^1$, is —NH—CO—$Q^1$, acylating an amine of formula II,

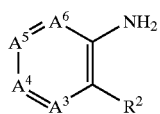

using a corresponding acid of formula HO—CO—$Q^1$, or an activated derivative thereof. Typical activated derivatives include the acid halides, activated esters, including 4-nitrophenyl esters and those derived from coupling reagents. Typical procedures include that described at Example 1-D.

(B) For a compound of formula I in which —$L^1$—$Q^1$ is —CO—NH—$Q^1$ and (preferably) at least one of $A^3$ and $A^5$ is N, substituting the group $Y^a$ of a compound of formula III

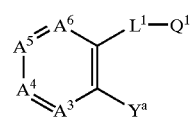

in which $Y^a$ is a conventional leaving group for nucleophilic aromatic substitution with an amine of formula $NH_2$—$CH_2$—$Q_2$. As used herein, a leaving group "$y^a$" is a moiety which is displaced in an aromatic (or heteroaromatic) nucleophilic substitution reaction, for example a halo group (such as fluoro or chloro), an alkoxy group (such as methoxy), a sulfonate ester group (such as methylsulfonyloxy, p-toluyl-sulfonyloxy or trifluoromethylsulfonyloxy), or the reactive species derived from treating an alcohol with triphenylphospine, diethyl azodicarboxylate and triethyl amine (in a Mitsunobu reaction). The substitution may be carried out by heating a mixture of the reagents in a polar solvent, for example in ethanol in a sealed tube as described at Example 8-B or in dimethylformamide with cuprous bromide as described at example 11-B for a compound in which neither of $A^3$ and $A^5$ is N, but only $A^4$ is N.

(C) For a compound of formula I in which —$L^1$—$Q^1$ is —CO—NH—$Q^1$, acylating an amine of formula $H_2N$—$Q^1$, or a deprotonated derivative thereof, using an acid of formula IV, or an activated derivative thereof.

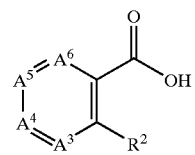

Typical deprotonated derivatives of the amine $H_2N$—$Q^1$ include, for example, that derived from treatment of the amine with an organomagnesium reagent, for example, with allylmagnesium bromide or methylmagnesium bromide. Typical activated derivatives include the acid halides, activated esters, including 4-nitrophenyl esters and those derived from coupling reagents. Preferably, the activated acid is an anhydride of formula IVb,

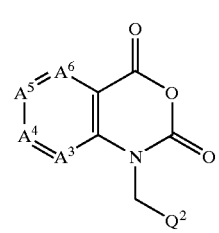

A typical procedure is that described at Example 12-B.

(D) Alkylating an amine of formula V

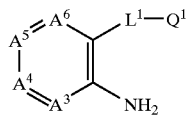

V directly, using a compound of formula Y—CH$_2$—Q$_2$, as described at Example 1-D, or (preferably) indirectly by reductive alkylation using an aldehyde of formula Q$^2$—CHO. In the reductive alkylation the intermediate imine of formula VT or acid addition salt thereof

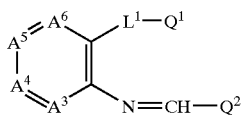

VI (which provide a further aspect of the invention) may be formed in situ and reduced directly, or may be isolated prior to reduction, for example as described at Example 14-E where the reduction is carried out using borane trimethylamine complex in glacial acetic acid.

(E) For a compound of formula I in which —L$^1$—Q$^1$ is —CH$_2$—NH—Q$^1$, reducing a corresponding compound of formula I in which —L$^1$—Q$^1$ is —CO—NH—Q$^1$, for example using lithium aluminum hydride in tetrahydrofuran as described at Example 9.

(F) For a compound of formula I in which R$^{2A}$ is methylsulfonyl, substituting the amino nitrogen of a corresponding compound of formula I in which R$^{2A}$ is hydrogen using an activated derivative of methanesulfonic acid, for example methanesulfonyl chloride in the presence of added base.

(G) For a compound of formula I in which R$^{2A}$ is —CHR$^y$R$^z$ or —CHR$^w$R$^x$, alkylating the amino nitrogen of a corresponding compound of formula I in which R$^{2A}$ is hydrogen using an alkylating agent of formula Y—CHR$^y$R$^z$ or Y—CHR$^w$R$^x$ or, preferably, reductively alkylating the amine using a compound of formula R$^y$—CO—R$^z$ or R$^w$—CO—R$^x$. The direct alkylation may be completed in a polar solvent in the presence of a base. The reductive alkylation conveniently is carried out, for example, using sodium cyanoborohydride in methanol/acetic acid as described at Example 14-G or using sodium triacetoxyborohydride in an inert solvent such as 1,2-dichloroethane along with an excess of the carbonyl compound and glacial acetic acid.

(H) For a compound of formula I in which R$^{2A}$ is 4-pyridinyl (which is unsubstituted or bears a substituent R$^v$ at the 2- or 3-position), substituting the amino nitrogen of a corresponding compound of formula I in which R$^{2A}$ is hydrogen using a corresponding pyridine reagent bearing a leaving group Y at the 4-position, for example with a 4-chloropyridine in ethanol.

(I) For a compound of formula I in which R$^{2A}$ is 4-pyridinyl in which R$^v$ is alkoxycarbonyl, esterifying a corresponding compound of formula I in which R$^v$ is carboxy.

(J) For a compound of formula I in which R$^{2A}$ is 4-pyridinyl in which R$^v$ is hydroxymethyl, reducing the ester of a corresponding compound of formula I in which R$^v$ is alkoxycarbonyl.

(K) For a compound of formula I in which R$^{2A}$ is 4-pyridinyl in which R$^v$ is carbamoyl, amidating the ester of a corresponding compound of formula I in which R$^v$ is alkoxycarbonyl.

(L) For a compound of formula I in which R$^{2A}$ is 4-pyridinyl in which R$^v$ is thiocarbamoyl, adding H$_2$S to the nitrile of a corresponding compound of formula I in which R$^v$ is cyano.

(M) For a compound of formula I in which R$^{2A}$ is 4-pyridinyl in which R$^v$ is N-hydroxyamidino, adding H$_2$NOH to the nitrile of a corresponding compound of formula I in which R$^v$ is cyano. The addition may be direct or indirect, such as via an imidate ester or by treating a compound in which R$^v$ is thiocarbamoyl with methyl iodide to form a thioimidate ester, then treatment with hydroxylamine.

(N) For a compound of formula I in which R$^{2A}$ is 4-pyridinyl in which R$^v$ is carboxy, decomposing the ester of a corresponding compound of formula I in which R$^v$ is alkoxycarbonyl.

(O) For a compound of formula I in which —NR$^s$R$^t$ is other than amino, alkylating a corresponding compound of formula I in which —NR$^s$R$^t$ is amino using a conventional method. When R$^s$ and R$^t$ together are trimethylene or tetramethylene, a difunctional alkylating agent, such as 1,3-dibromopropane or 1,4-dibromobutane is preferred.

(P) For a compound of formula I which bears —NR$^s$R$^t$, reductively alkylating X—NR$^s$R$^t$ using a corresponding compound but in which the carbon to bear the —NR$^s$R$^t$ group bears an oxo group, for example, using a procedure similar to one of procedure (G) above.

(Q) For a compound of formula I in which R$^p$ is 1-hydroxy-1-methylethyl, adding a methyl group to the carbonyl group of a corresponding compound of formula I in which R$^p$ is acetyl using an organometallic reagent such as, for example, methylmagnesium bromide.

(R) For a compound of formula I in which R$^p$ is 1-methoxy-1-methylethyl, treating a corresponding compound of formula I in which R$^p$ is 1-hydroxy-1-methylethyl with methanol and an acid catalyst.

(S) For a compound of formula I in which R$^4$ or R$^5$ is amino, reducing the nitro group of a compound corresponding to a compound of formula I but in which R$^4$ or R$^5$ is nitro.

(T) For a compound of formula I in which R$^4$ or R$^5$ is R$^g$NH— and R$^g$ is R$^h$SO$_2$—, substituting the amino group of a corresponding compound of formula I in which R$^4$ or R$^5$ is amino using an activated derivative of the sulfonic acid R$^h$SO$_2$—OH.

Whereafter, for any of the above procedures, when a functional group is protected using a protecting group, removing the protecting group.

Whereafter, for any of the above procedures, when a pharmaceutically acceptable salt of a compound of formula I is required, it is obtained by reacting the basic form of a basic compound of formula I with an acid affording a physiologically acceptable counterion or the acidic form of an acidic compound of formula I with a base affording a physiologically acceptable counterion or by any other conventional procedure.

A novel intermediate or starting material compound such as, for example, a novel compound of formula II, III, IV or VI, etc., provides a further aspect of the invention. The various starting material may be made by processes which include processes known in the chemical art for the production of structurally analogous compounds or by a novel process described herein or one analogous thereto.

As mentioned above, a compound corresponding to a compound of formula I but in which a functional group is protected may serve as an intermediate for a compound of formula I. Accordingly, such a protected intermediate for a novel compound of formula I provides a further aspect of the invention. Thus, as one particular aspect of the invention, there is provided a compound corresponding to a novel compound of formula I as defined above in which $R^4$ is hydroxy, but in which the corresponding substituent is —$OP^p$ in place of hydroxy, wherein $P^p$ is a phenol protecting group other than (1–4C)alkyl or benzyl. Phenol protecting groups are well known in the art, for example as described in T. W. Greene and P. G. M. Wuts, "Protecting Groups in Organic Synthesis" (1991). Further, $P^p$ may denote a functionalized resin, for example as disclosed in H. V. Meyers, et al., *Molecular Diversity*, (1995), 1, 13–20.

As mentioned above, the invention includes a pharmaceutically acceptable salt of the factor Xa inhibiting compound defined by the above formula I. A basic compound of this invention possesses one or more functional groups sufficiently basic to react with any of a number of inorganic and organic acids affording a physiologically acceptable counterion to form a pharmaceutically acceptable salt. Acids commonly employed to form pharmaceutically acceptable acid addition salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromobenzenesulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts include those formed with mineral acids such as hydrochloric acid, hydrobromic acid and sulfuric acid.

For a compound of formula I which bears an acidic moiety, such as a carboxy group, a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as triethylamine, morpholine, piperidine and triethanolamine.

If not commercially available, a necessary starting material for the preparation of a compound of formula I may be prepared by a procedure which is selected from standard techniques of organic chemistry, including aromatic and heteroaromatic substitution and transformation, from techniques which are analogous to the syntheses of known, structurally similar compounds, and techniques which are analogous to the above described procedures or procedures described in the Examples. It will be clear to one skilled in the art that a variety of sequences is available for the preparation of the starting materials. Starting materials which are novel provide another aspect of the invention.

Selective methods of substitution, protection and deprotection are well known in the art for preparation of a compound such as one of formula II, III, IV or VI discussed above.

Generally, a basic compound of the invention is isolated best in the form of an acid addition salt. A salt of a compound of formula I formed with an acid such as one of those mentioned above is useful as a pharmaceutically acceptable salt for administration of the antithrombotic agent and for preparation of a formulation of the agent. Other acid addition salts may be prepared and used in the isolation and purification of the compounds.

As noted above, the optically active isomers and diastereomers of the compounds of formula I are also considered part of this invention. Such optically active isomers may be prepared from their respective optically active precursors by the procedures described above, or by resolving the racemic mixtures. This resolution can be carried out by derivatization with a chiral reagent followed by chromatography or by repeated crystallization. Removal of the chiral auxiliary by standard methods affords substantially optically pure isomers of the compounds of the present invention or their precursors. Further details regarding resolutions can be obtained in Jacques, et al., *Enantiomers, Racemates, and Resolutions*, John Wiley & Sons, 1981.

The compounds of the invention are believed to selectively inhibit factor Xa over other proteinases and nonenzyme proteins involved in blood coagulation without appreciable interference with the body, natural clot lysing ability (the compounds have a low inhibitory effect on fibrinolysis). Further, such selectivity is believed to permit use with thrombolytic agents without substantial interference with thrombolysis and fibrinolysis.

The invention in one of its aspects provides a method of inhibiting factor Xa in mammals comprising administering to a mammal in need of treatment an effective (factor Xa inhibiting) dose of a compound of formula I.

In another of its aspects, the invention provides a method of treating a thromboembolic disorder comprising administering to a mammal in need of treatment an effective (thromboembolic disorder therapeutic and/or prophylactic amount) dose of a compound of formula I.

The invention in another of its aspects provides a method of inhibiting coagulation in a mammal comprising administering to a mammal in need of treatment an effective (coagulation inhibiting) dose of a compound of formula I.

The factor Xa inhibition, coagulation inhibition and thromboembolic disorder treatment contemplated by the present method includes both medical therapeutic and/or prophylactic treatment as appropriate.

In a further embodiment, the invention relates to treatment, in a human or animal, of a condition where inhibition of factor Xa is required. The compounds of the invention are expected to be useful in mammals, including man, in treatment or prophylaxis of thrombosis and hypercoagulability in blood and tissues. Disorders in which the compounds have a potential utility are in treatment or prophylaxis of thrombosis and hypercoagulability in blood and tissues. Disorders in which the compounds have a potential utility, in treatment and/or prophylaxis, include venous thrombosis and pulmonary embolism, arterial thrombosis, such as in myocardial ischemia, myocardial infarction, unstable angina, thrombosis-based stroke and peripheral arterial thrombosis. Further, the compounds have expected utility in the treatment or prophylaxis of atherosclerotic disorders (diseases) such as coronary arterial disease, cerebral arterial disease and peripheral arterial disease. Further, the compounds are expected to be useful together with thrombolytics in myocardial infarction. Further, the compounds have expected utility in prophylaxis for reocclusion after thrombolysis, percutaneous transluminal angioplasty (PTCA) and coronary bypass operations. Further, the compounds have expected utility in prevention of rethrombosis after microsurgery. Further, the compounds are expected to be useful in anticoagulant treatment in connection with artificial organs, including joint replacement, and cardiac valves. Further, the compounds have expected utility in anticoagulant treatment in hemodialysis and disseminated intravascular coagulation. A further expected utility is in rinsing of catheters and mechanical devices used in patients in vivo, and as an anticoagulant for preservation of blood, plasma and other blood products in vitro. Still further, the compounds have expected utility in other diseases where blood coagulation could be a fundamental contributing process or a source of secondary pathology, such as cancer, including metastasis, inflammatory diseases, including arthritis, and diabetes. The anticoagulant compound is administered orally or parenterally, e.g. by intravenous infusion (iv), intramuscular injection (im) or subcutaneously (sc).

The specific dose of a compound administered according to this invention to obtain therapeutic and/or prophylactic effects will, of course, be determined by the particular circumstances surrounding the case, including, for example, the compound administered, the rate of administration, the route of administration, and the condition being treated.

A typical daily dose for each of the above utilities is between about 0.01 mg/kg and about 1000 mg/kg. The dose regimen may vary e.g. for prophylactic use a single daily dose may be administered or multiple doses such as 3 or 5 times daily may be appropriate. In critical care situations a compound of the invention is administered by iv infusion at a rate between about 0.01 mg/kg/h and about 20 mg/kg/h and preferably between about 0.1 mg/kg/h and about 5 mg/kg/h.

The method of this invention also is practiced in conjunction with a clot lysing agent e.g. tissue plasminogen activator (t-PA), modified t-PA, streptokinase or urokinase. In cases when clot formation has occurred and an artery or vein is blocked, either partially or totally, a clot lysing agent is usually employed. A compound of the invention can be administered prior to or along with the lysing agent or subsequent to its use, and preferably further is administered along with aspirin to prevent the reoccurrence of clot formation.

The method of this invention is also practiced in conjunction with a platelet glycoprotein receptor (IIb/IIIa) antagonist, that inhibits platelet aggregation. A compound of the invention can be administered prior to or along with the IIb/IIIa antagonist or subsequent to its use to prevent the occurrence or reoccurrence of clot formation.

The method of this invention is also practiced in conjunction with aspirin. A compound of the invention can be administered prior to or along with aspirin or subsequent to its use to prevent the occurrence or reoccurrence of clot formation. As stated above, preferably a compound of the present invention is administered in conjunction with a clot lysing agent and aspirin.

This invention also provides a pharmaceutical composition for use in the above described therapeutic method. A pharmaceutical composition of the invention comprises an effective factor Xa inhibiting amount of a compound of formula I in association with a pharmaceutically acceptable carrier, excipient or diluent.

The active ingredient in such formulations comprises from 0.1 percent to 99.9 percent by weight of the formulation. By pharmaceutically acceptable it is meant the carrier, diluent or excipient must be compatible with the other ingredients of the formulation and not deleterious to the recipient thereof.

For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent e.g. physiological saline (0.9 percent), 5 percent dextrose, Ringer's solution and the like.

The compound of the present invention can be formulated in unit dosage formulations comprising a dose between about 0.1 mg and about 1000 mg. Preferably the compound is in the form of a pharmaceutically acceptable salt such as for example the sulfate salt, acetate salt or a phosphate salt. An example of a unit dosage formulation comprises 5 mg of a compound of the present invention as a pharmaceutically acceptable salt in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The compounds can be administered by a variety of routes including oral, rectal, transdermal, subcutaneous, intravenous, intramuscular, and intranasal. The compounds of the present invention are preferably formulated prior to administration.

The present pharmaceutical compositions are prepared by known procedures using well known and readily available ingredients. The compositions of this invention may be formulated so as to provide quick, sustained, or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), soft and hard gelatin capsules, suppositories, sterile injectable solutions, sterile packaged powders, and the like.

The following formulation examples are illustrative only and are not intended to limit the scope of the invention in any way. "Active ingredient", of course, means a compound according to formula I or a pharmaceutically acceptable salt or solvate thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
| --- | --- |
| Active ingredient | 0.25 |
| Ethanol | 29.75 |
| propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| Active ingredient | 60 mg |
| --- | --- |
| Starch | 45 mg |
| Microcrystalline cellulose | 35 mg |
| polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| Active ingredient | 80 mg |
| --- | --- |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient | 225 mg |
| --- | --- |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 mL dose, are made as follows:.

| Active ingredient | 50 mg |
| --- | --- |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg |
| --- | --- |
| Isotonic saline | 1,000 mL |

The solution of the above ingredients generally is administered intravenously to a subject at a rate of 1 mL per minute.

The ability of a compound of the present invention to be an effective and orally active factor Xa inhibitor may be evaluated in one or more of the following assays or in other standard assays known to those in the art.

The inhibition by a compound of the inhibition of a serine protease of the human blood coagulation system or of the fibrinolytic system, as well as of trypsin, is determined in vitro for the particular enzyme by measuring its inhibitor binding affinity in an assay in which the enzyme hydrolyzes a particular chromogenic substrate, for example as described in Smith, G. F.; Gifford-Moore, D.; Craft, T. J.; Chirgadze, N.; Ruterbories, K. J.; Lindstrom, T. D.; Satterwhite, J. H. Efegatran: A New Cardiovascular Anticoagulant. *New Anticoagulants for the Cardiovascular Patient*; Pifarre, R., Ed.; Hanley & Belfus, Inc.: Philadelphia, 1997; pp. 265–300. The inhibitor binding affinity is measured as apparent association constant Kass which is the hypothetical equilibrium constant for the reaction between enzyme and the test inhibitor compound (I).

$$\text{Enzyme} + I \rightleftharpoons \text{Enzyme} - I$$

$$Kass = \frac{[\text{Enzyme} - I]}{[(\text{Enzyme}) \times (I)]}$$

Conveniently, enzyme inhibition kinetics are performed in 96-well polystyrene plates and reaction rates are determined from the rate of hydrolysis of appropriate p-nitroanilide substrates at 405 nm using a Thermomax plate reader from Molecular Devices (San Francisco, Calif.). The same protocol is followed for all enzymes studied: 50 µL buffer (0.03 M Tris, 0.15 M NaCl pH 7) in each well, followed by 25 µL of inhibitor solution (in 100% methanol, or in 50% v:v aqueous methanol) and 25 µL enzyme solution; within two minutes, 150 µL aqueous solution of chromogenic substrate (0.25 mg/mL) is added to start the enzymatic reaction. The rates of chromogenic substrate hydrolysis reactions provide a linear relationship with the enzymes studied such that free enzyme can be quantitated in reaction mixtures. Data is analyzed directly as rates by the Softmax program to produce [free enzyme] calculations for tight-binding Kass determinations. For apparent Kass determinations, 1.34 nM human factor Xa is used to hydrolyze 0.18 mM BzIle-Glu-Gly-Arg-pNA; 5.9 nM human thrombin or 1.4 nM bovine trypsin is used to hydrolyze 0.2 mM BzPhe-Val-Arg-pNA; 3.4 nM human plasmin is used with 0.5 mM HD-Val-Leu-Lys-pNA; 1.2 nM human nt-PA is used with 0.81 mM HD-Ile-Pro-Arg-pNA; and 0.37 nM urokinase is used with 0.30 mM pyro-gfsGlu-Gly-Arg-pNA.

Kass is calculated for a range of concentrations of test compounds and the mean value reported in units of liter per mole. In general, a factor Xa inhibiting compound of formula I of the instant invention, as exemplified herein, exhibits a Kass of 0.1 to $0.5 \times 10^6$ L/mole or much greater.

The factor Xa inhibitor preferably should spare fibrinolysis induced by urokinase, tissue plasminogen activator (t-PA) and streptokinase. This would be important to the therapeutic use of such an agent as an adjunct to streptokinase, tp-PA or urokinase thrombolytic therapy and to the use of such an agent as an endogenous fibrinolysis-sparing (with respect to t-PA and urokinase) antithrombotic agent. In addition to the lack of interference with the amidase activity of the fibrinolytic proteases, such fibrinolytic system sparing can be studied by the use of human plasma clots and their lysis by the respective fibrinolytic plasminogen activators.

Materials

Dog plasma is obtained from conscious mixed-breed hounds (either sex Butler Farms, Clyde, N.Y., U.S.A.) by venipuncture into 3.8 percent citrate. Fibrinogen is prepared from fresh dog plasma and human fibrinogen is prepared from in-date ACD human blood at the fraction I-2 according to previous procedures and specification. Smith, *Biochem. J.*, 185, 1–11 (1980; and Smith, et al., *Biochemistry*, 11, 2958–2967, (1972). Human fibrinogen (98 percent pure/plasmin free) is from American Diagnostica, Greenwich, Conn. Radiolabeling of fibrinogen I-2 preparations is performed as previously reported. Smith, et al., *Biochemistry*, 11, 2958–2967, (1972). Urokinase is purchased from Leo Pharmaceuticals, Denmark, as 2200 Ploug units/vial. Streptokinase is purchased from Hoechst-Roussel Pharmaceuticals, Somerville, N.J.

Methods—Effects on Lysis of Human Plasma Clots by t-PA

Human plasma clots are formed in micro test tubes by adding 50 µL thrombin (73 NIH unit/mL) to 100 µL human plasma which contains 0.0229 µCi 125-iodine labeled fibrinogen. Clot lysis is studied by overlaying the clots with 50 µL of urokinase or streptokinase (50, 100, or 1000 unit/mL) and incubating for 20 hours at room temperature. After incubation the tubes are centrifuged in a Beckman Microfuge. 25 µL of supernate is added into 1.0 mL volume of 0.03 M tris/0.15 M NaCl buffer for gamma counting. Counting controls 100 percent lysis are obtained by omitting thrambin (and substituting buffer). The factor Xa inhibitors are evaluated for possible interference with fibrinolysis by including the compounds in the overlay solutions at 1, 5, and 10 µg/mL concentrations. Rough approximations of $IC_{50}$ values are estimated by linear extrapolations from data points to a value which would represent 50 percent of lysis for that particular concentration of fibrinolytic agent.

Anticoagulant Activity

Materials

Dog plasma and rat plasma are obtained from conscious mixed-breed hounds (either sex, Butler Farms, Clyde, N.Y., U.S.A.) or from anesthetized male Sprague-Dawley rats (Harlan Sprague-Dawley, Inc., Indianapolis, Ind., U.S.A.) by venipuncture into 3.8 percent citrate. Fibrinogen is prepared from in-date ACD human blood as the fraction I-2 according to previous procedures and specifications. Smith, *Biochem. J.*, 185, 1–11 (1980); and Smith, et al., *Biochemistry*, 11, 2959–2967 (1972). Human fibrinogen is also purchased as 98 percent pure/plasmin free from American Diagnostica, Greenwich, Conn. Coagulation reagents Actin, Thromboplastin, Innovin and Human plasma are from Baxter Healthcare Corp., Dade Division, Miami, Fla. Bovine thrombin from Parke-Davis (Detroit, Mich.) is used for coagulation assays in plasma.

Methods

Anticoagulation Determinations

Coagulation assay procedures are as previously described. Smith, et al., *Thrombosis Research*, 50, 163–174 (1988). A CoAScreener coagulation instrument (American LABor, Inc.) is used for all coagulation assay measurements. The prothrombin time (PT) is measured by adding 0.05 mL saline and 0.05 mL Thromboplastin-C reagent or recombinant human tissue factor reagent (Innovin) to 0.05 mL test plasma. The activated partial thromboplastin time (APTT) is measured by incubation of 0.05 mL test plasma with 0.05 mL Actin reagent for 120 seconds followed by 0.05 mL $CaCl_2$ (0.02 M). The thrombin time (TT) is measured by adding 0.05 mL saline and 0.05 mL thrombin (10 NIH units/mL) to 0.05 mL test plasma. The compounds of formula I are added to human or animal plasma over a wide range of concentrations to determine prolongation effects on the APTT, PT, and TT assays. Linear extrapolations are performed to estimate the concentrations required to double the clotting time for each assay.

Animals

Male Sprague Dawley rats (350–425 gm, Harlan Sprague Dawley Inc., Indianapolis, Ind.) are anesthetized with xylazine (20 mg/kg, s.c.) and ketamine (120 mg/kg, s.c.) and maintained on a heated water blanket (37° C.). The jugular vein(s) is cannulated to allow for infusions.

Arterio-Venous Shunt Model

The left jugular vein and right carotid artery are cannulated with 20 cm lengths of polyethylene PE 60 tubing. A 6 cm center section of larger tubing (PE 190) with a cotton thread (5 cm) in the lumen, is friction fitted between the longer sections to complete the arterio-venous shunt circuit. Blood is circulated through the shunt for 15 min before the thread is carefully removed and weighed. The weight of a wet thread is subtracted from the total weight of the thread and thrombus (see J. R. Smith, *Br J Pharmacol*, 77:29, 1982).

FeCl$_3$ Model of Arterial Injury

The carotid arteries are isolated via a midline ventral cervical incision. A thermocouple is placed under each artery and vessel temperature is recorded continuously on a strip chart recorder. A cuff of tubing (0.058 ID×0.077 OD×4 mm, Baxter Ned. Grade Silicone), cut longitudinally, is placed around each carotid directly above the thermocouple. FeCl$_3$ hexahydrate is dissolved in water and the concentration (20 percent) is expressed in terms of the actual weight of FeCl$_3$ only. To injure the artery and induce thrombosis, 2.85 $\mu$L is pipetted into the cuff to bathe the artery above the thermocouple probe. Arterial occlusion is indicated by a rapid drop in temperature. The time to occlusion is reported in minutes and represents the elapsed time between application of FeCl$_3$ and the rapid drop in vessel temperature (see K. D. Kurz, *Thromb. Res.*, 60:269, 1990).

Coagulation Parameters

Plasma thrombin time (TT) and activated partial thromboplastin time (APTT) are measured with a fibrometer. Blood is sampled from a jugular catheter and collected in syringe containing sodium citrate (3.8 percent, 1 part to 9 parts blood). To measure TT, rat plasma (0.1 mL) is mixed with saline (0.1 mL) and bovine thrombin (0.1 mL, 30 UmL in TRIS buffer; Parke Davis) at 37° C. For APTT, plasma (0.1 mL) and APTT solution (0.1 mL, Organon Teknika) are incubated for 5 minutes (37° C.) and CaCl$_2$ (0.1 mL, 0.025 M) is added to start coagulation. Assays are done in duplicate and averaged.

Index of Bioavailability

Bioavailability studies may be conducted as follows. Compounds are administered as aqueous solutions to male Fisher rats, intravenously (iv) at 5 mg/kg via tail vein injection and orally (po) to fasted animals at 20 mg/kg by gavage. Serial blood samples are obtained at 5, 30, 120, and 240 minutes postdose following intravenous administration and at 1, 2, 4, and 6 hours after oral dosing. Plasma is analyzed for drug concentration using an HPLC procedure involving CB Bond Elute (Varion) cartridges for sample preparation and a methanol/30 nM ammonium acetate buffer (pH 4) gradient optimized for each compound. % Oral bioavailability is calculated by the following equation:

$$\% \text{ Oral bioavailability} = \frac{AUC\ po}{AUV\ iv} \times \frac{\text{Dose } iv}{\text{Dose } po} \times 100$$

where AUC is area under the curve calculated from the plasma level of compound over the time course of the experiment following oral (AUC po) and intravenous (AUC iv) dosing.

Compounds

Compound solutions are prepared fresh daily in normal saline and are injected as a bolus or are infused starting 15 minutes before and continuing throughout the experimental perturbation which is 15 minutes in the arteriovenous shunt model and 60 minutes in the FeCl$_3$ model of arterial injury and in the spontaneous thrombolysis model. Bolus injection volume is 1 mL/kg for i.v., and 5 mL/kg for p.o., and infusion volume is 3 mL/hr.

Statistics

Results are expressed as means+/−SEM. One-way analysis of variance is used to detect statistically significant differences and then Dunnett's test is applied to determine which means are different. Significance level for rejection of the null hypothesis of equal means is P<0.05.

Animals

Male dogs (Beagles; 18 months–2 years; 12–13 kg, Marshall Farms, North Rose, N.Y. 14516) are fasted overnight and fed Purina certified Prescription Diet (Purina Mills, St. Louis, Mo.) 240 minutes after dosing. Water is available ad libitum. The room temperature is maintained between 66–74° F.; 45–50 percent relative humidity, and lighted from 0600–1800 hours.

Pharmacokinetic Model

Test compound is formulated immediately prior to dosing by dissolving in sterile 0.9 percent saline to a 5 mg/mL preparation. Dogs are given a single 2 mg/kg dose of test compound by oral gavage. Blood samples (4.5 mL) are taken from the cephalic vein at 0.25, 0.5, 0.75, 1, 2, 3, 4 and 6 hours after dosing. Samples are collected in citrated Vacutainer tubes and kept on ice prior to reduction to plasma by centrifugation. Plasma samples are analyzed by HPLC MS. Plasma concentration of test compound is recorded and used to calculate the pharmacokinetic parameters; elimination rate constant, Ke; total clearance, Clt; volume of distribution, V$_D$; time of maximum plasma test compound concentration, Tmax; maximum concentration of test compound of Tmax, Cmax; plasma half-life, t0.5; and area under the curve, A.U.C.; fraction of test compound absorbed, F.

Canine Model of Coronary Artery Thrombosis

Surgical preparation and instrumentation of the dogs are as described in Jackson, et al., *Circulation*, 82, 930–940 (1990). Mixed-breed hounds (aged 6–7 months, either Bex, Butler Farms, Clyde, N.Y., U.S.A.) are anesthetized with sodium pentobarbital (30 mg/kg intravenously, i.v.), incubated, and ventilated with room air. Tidal volume and respiratory rates are adjusted to maintain blood PO$_2$, PCO$_2$, and pH within normal limits. Subdermal needle electrodes are inserted for the recording of a lead II ECG. The left jugular vein and common carotid artery are isolated through a left mediolateral neck incision. Arterial blood pressure (ABP) is measured continuously with a precalibrated Millar transducer (model (MPC-500, Millar Instruments, Houston, Tex., U.S.A.) inserted into the carotid artery. The a jugular vein is cannulated for blood sampling during the experiment. In addition, the femoral veins of both hindlegs are cannulated for administration of test compound.

A left thoracotomy is performed at the fifth intercostal space, and the heart is suspended in a pericardial cradle. A 1- to 2-cm segment of the left circumflex coronary artery (LCX) is isolated proximal to the first major diagonal ventricular branch. A 26-gauge needle-tipped wire anodal electrode (Teflon-coated, 30-gauge silverplated copper wire) 3–4 mm long is inserted into the LCX and placed in contact with the intimal surface of the artery (confirmed at the end of the experiment) The stimulating circuit is completed by placing the cathode in a subcutaneous (s.c.) site. An adjustable plastic occluder is placed around the LCX, over the region of the electrode. A precalibrated electromagnetic flow probe (Carolina Medical Electronics, King, N.C., U.S.A.) is placed around the LCX proximal to the anode for measurement of coronary blood flow (CBF). The occluder is adjusted to produce a 40–50 percent inhibition of the hyperemic blood flow response observed after 10-s mechanical occlusion of the LCX. All hemodynamic and EM measurements are recorded and analyzed with a data acquisition system (model M3000, Modular Instruments, Malvern, Pa. U.S.A.).

Thrombus Formation and Compound Administration Regimens

Electrolytic injury of the intima of the LCX is produced by applying 100-μA direct current (DC) to the anode. The current is maintained for 60 min and then discontinued whether the vessel has occluded or not. Thrombus formation proceeds spontaneously until the LCX is totally occluded (determined as zero CBF and an increase in the S-T segment). Compound administration is started after the occluding thrombus is allowed to age for 1 hour. A 2-hour infusion of the compounds of the present invention at doses of 0.5 and 1 mg/kg/hour is begun simultaneously with an infusion of thrombolytic agent (e.g. tissue plasminogen activator, streptokinase, APSAC). Reperfusion is followed for 3 hour after administration of test compound. Reocclusion of coronary arteries after successful thrombolysis is defined as zero CBF which persisted for at least 30 minutes.

Hematology and Template Bleeding Time Determinations

Whole blood cell counts, hemoglobin, and hematocrit values are determined on a 40-μL sample of citrated (3.8 percent) blood (1 part citrate:9 parts blood) with a hematology analyzer (Cell-Dyn 900, Sequoia-Turner. Mount View, Calif., U.S.A.). Gingival template bleeding times are determined with a Simplate II bleeding time device (Organon Teknika Durham, N.C., U.S.A.). The device is used to make 2 horizontal incisions in the gingiva of either the upper or lower left jaw of the dog. Each incision is 3 mm wide×2 mm deep. The incisions are made, and a stopwatch is used to determine how long bleeding occurs. A cotton swab is used to soak up the blood as it oozes from the incision. Template bleeding time is the time from incision to stoppage of bleeding. Bleeding times are taken just before administration of test compound (0 min), 60 min into infusion, at conclusion of administration of the test compound (120 min), and at the end of the experiment.

All data are analyzed by one-way analysis of variance (ANOVA) followed by Student-Neuman-Kuels post hoc t test to determine the level of significance. Repeated-measures ANOVA are used to determine significant differences between time points during the experiments. Values are determined to be statistically different at least at the level of p<0.05. All values are mean±SEM. All studies are conducted in accordance with the guiding principles of the American Physiological Society. Further details regarding the procedures are described in Jackson, et al., *J. Cardiovasc. Pharmacol.*, (1993), 21, 587–599.

The following Examples are provided to further describe the invention and are not to be construed as limitations thereof.

The abbreviations, symbols and terms used in the examples have the following meanings.

Ac=acetyl
Boc=t-butyloxycarbonyl
Calcd=calculated
conc=concentrated
DMF=dimethylformamide
DMSO=dimethylsulfoxide
Et=ethyl
EtOAc=ethyl acetate
EtOH=ethanol
FTIR=Fourier transform IR
HPLC=High Performance Liquid Chromatography
HRMS=high resolution mass spectrum
i-PrOH=isopropanol
IR=Infrared Spectrum
LAH=lithium aluminum hydride
LC-MS=liquid chromatography-mass spectrum (using HPLC)
Me=methyl
MeOH=methanol
MS-ES (or ES-MS)=electrospray mass spectrum
MS-FAB (or FAB-MS)=fast atom bombardment mass spectrum
MS-FIA (or FIA-MS)=flow injection analysis mass spectrum
MS-FD (or FD-MS)=field desorption mass spectrum
MS-IS (or IS-MS)=ion spray mass spectrum
NMR=Nuclear Magnetic Resonance
Ph=phenyl
i-Pr=isopropyl
RPHPLC=Reversed Phase High Performance Liquid Chromatography
RT (or $R_t$)=retention time
satd=saturated
$SiO_2$=silica gel
SCX=strong cation exchange (resin)
TFA=trifluoroacetic acid
THF=tetrahydrofuran
TLC=thin layer chromatography Unless otherwise stated, pH adjustments and work up are with aqueous acid or base solutions. $^1$H-NMR indicates a satisfactory NMR spectrum was obtained for the compound described. IR (or FTIR) indicates a satisfactory infra red spectrum was obtained for the compound described.

EXAMPLE 1

Preparation of $N^1$-(4-Methoxybenzoyl)-$N^2$-[4-(4-morpholinyl)-benzyl]-1,2-benzenediamine

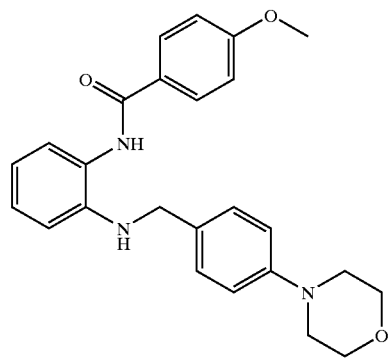

A. 4-(4-morpholinyl)benzonitrile

A solution of 4-fluorobenzonitrile (1.00 g, 8.26mmol) and morpholine (0.77 mL, 9.08 mmol) in dimethyl sulfoxide (40 mL) was treated with 37% KF on alumina, and the mixture was heated at 150° C. for 5 h. After cooling, the mixture was diluted with EtOAc and filtered through diatomaceous earth. The filtrate was washed with water (3×), brine (1×), and then dried with magnesium sulfate. The extract was concentrated and the residue was purified by chromatography ($SiO_2$, 20 to 30% EtOAc in hexanes) yielding 930 mg (60%) of the title compound.

B. 4-(4-morpholinyl)benzoic Acid

A solution of 4-(4-morpholinyl)benzonitrile (930 mg, 5.00 mmol) in 1:1 dioxane:water (20 mL) was treated with potassium hydroxide (1.12 g. 20 mmol). The mixture was heated at reflux for 96 h, concentrated, and the residue was dissolved in water. Upon acidification (pH~2–3), a white precipitate resulted which was collected by filtration yielding 1.21 g (99%) of the title compound.

$^1$NMR

C. 4-(4-morpholinyl)benzyl Alcohol

A solution of 4-(4-morpholinyl)benzoic acid (1.00 g, 4.83 mmol) and 4-methylmorpholine (0.53 mL, 4.8 mmol) in tetrahydrofuran (25 mL) at −10° C. was treated with ethyl chloroformate (0.46 mL, 4.8 mmol). After 0.25 h, the mixture was treated with sodium borohydride (550 mg, 14.5 mmol) followed by MeOH (50 mL) slowly. The mixture was then treated with 5% HOAC in water and the mixture was concentrated. The residue was purified by chromatography (SiO$_2$, EtOAc:hexanes) yielding 164 mg (18%) of the title compound.

$^1$NMR, IR

FD-MS, m/e 193 (m)

Analysis for $C_{11}H_{15}NO_2$:

| Calcd: | C, 68.37; | H, 7.82; | N, 7.25; |
|---|---|---|---|
| Found: | C, 68.46; | H, 7.95; | N, 7.21. |

D. $N^1$-(4-methoxybenzoyl)-$N^2$-[4-(4-morpholinyl)benzyl]-1,2-benzenediamine 4-(4-Morpholinyl)benzyl alcohol (150 mg, 0.78 mmol) was added to a solution of phosgene in toluene (1.93 M, 1.2 mL). After 4 h, the mixture was treated with a solution of $N^1$-(4-methoxybenzoyl)-1,2-benzenediamine (188 mg, 0.78 mmol) and pyridine (2 mL) in methylene chloride (3 mL). After 16 h, the mixture was concentrated and the residue was dissolved in EtOAc. The organic layer was washed with water (4×), brine (1×), dried with potassium carbonate, and concentrated. The residue was purified by chromatography (SiO$_2$, 5 to 15% EtOAc in CH$_2$Cl$_2$), yielding 45 mg (14%) of the title compound.

$^1$NMR, IR

FD-MS, m/e 417 (m)

Analysis for $C_{25}H_{27}N_3O_3$:

| Calcd: | C, 71.92; | H, 6.52; | N, 10.06; |
|---|---|---|---|
| Found: | C, 72.12; | H, 6.63; | N, 10.11. |

EXAMPLE 2

Preparation of $N^1$-(4-Methoxybenzoyl)-$N^2$-[1-(4-pyridyl)piperidin-4-ylmethyl]-1,2-benzendiamine

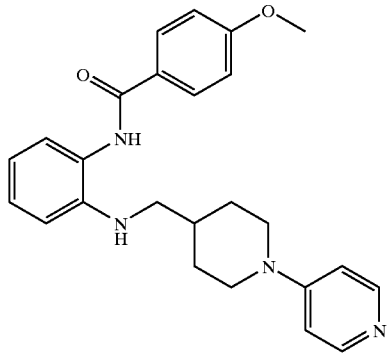

A. 1-(4-pyridyl)piperidine-4-methylamine 1-(4-Pyridyl)piperidine-4-methanol was prepared using a procedure similar to the following: A solution of methyl N-(4-pyridyl)isonipecotate (600 mg, 2.72 mmol) in tetrahydrofuran was added to a solution of lithium aluminum hydride (100 mg) in tetrahydrofuran (14 mL) cooled to 0° C. Upon consumption of the starting material (0.5–2 h), the mixture was treated with water (0.10 mL), 15% aqueous sodium hydroxide (0.10 mL), and water (0.30 mL). After 0.25 h, the mixture was sonicated for 0.25 h, then poured into a mixture of ethyl acetate, water, sodium tartrate, and potassium tartrate. The aqueous layer was extracted twice with ethyl acetate and the combined extracts were dried (magnesium sulfate), filtered, and concentrated in vacuo to yield 357 mg,(68%) of 1-(4-pyridyl)piperidine-4-methanol, which was used without further purification.

$^1$H-NMR

A solution of 1-(4-pyridyl)piperidine-4-methanol (5.87 g, 30.6 mmol), phthalimide (4.59 g, 31.2 mmol), and triphenylphosphine (8.10 g, 30.9 mmol) in 125 mL of THF at −5° C. was treated with a solution of diethyl azodicarboxylate (5.38 g, 30.9 mmol) in THF (40 mL). After 16 h. the mixture was poured into EtOAc and 1 N HCl. The aqueous layer was washed with EtOAc (2×), pH adjusted to 12 by addition of 5 N NaOH, and washed with EtOAc (3×). The combined organic extracts were dried (K$_2$CO$_3$) and concentrated, yielding 8.45 g (86%). The crude material (5.47 g, 17.0 mmol) was then treated with hydrazine hydrate (3.5 mL, 60.0 mmol) in EtOH (50 mL). The mixture was heated at 75° C. for 5 h, cooled, diluted with CH$_2$Cl$_2$ (100 mL), and cooled to 0° C. The solid was removed by filtration; and the filtrate was concentrated, yielding 3.32 g of the title compound which was used without further purification.

$^1$H-NMR, IR

FD-MS, m/e 191 (m)

B. 2-nitro-N-[1-(4-pyridyl)piperidin-4-ylmethyl]aniline

A solution of 2-fluoronitrobenzene (0.13 mL, 1.3 mmol) and 1-(4-pyridyl)piperidine-4-methylamine (242 mg, 1.27 mmol) in DMF (5 mL) was treated with potassium carbonate (175 mg, 1.3 mmol). After 16 h, the mixture was diluted with EtOAc, the organic layer was washed with water (3×), brine, dried with K$_2$CO$_3$, and concentrated. The residue was dissolved in 5% HOAC in MEOH and loaded onto an SCX ion exchange column. Elution with MeOH followed by 2 M NH$_3$ in MeOH yielded 200 mg of the title compound; which was used without further purification.

$^1$NMR

C. $N^1$-[1-(4-pyridyl)piperidin-4-ylmethyl]-1,2-benzenediamine

A mixture of 2-nitro-N-[1-(4-pyridyl)piperidin-4-ylmethyl]aniline (235 mg, 0.75 mmol) and 10% palladium on carbon (200 mg) in ethanol (4 mL) was placed under an atmosphere of hydrogen gas. After 1 h, the mixture was filtered through diatomaceous earth. The filtrate was concentrated yielding 212 mg of the title compound, which was used without further purification.

$^1$NMR

D. $N^1$-(4-methoxybenzoyl)-$N^2$-[1-(4-pyridyl)piperidin-4-ylmethyl]-1,2-benzendiamine A solution of $N^1$-[1-(4-pyridyl)piperidin-4-ylmethyl]-1,2-benzenediamine (212 mg, 0.75mmol) and pyridine (4 mL) in chloroform (2 mL) at 0° C. was treated with a solution of 4-methoxybenzoyl chloride (128 mg, 0.75 mmol) in chloroform. The mixture was allowed to warm to room temperature and stir for 17 h. The mixture was concentrated and the residue was dissolved in EtOAc. The organic layer was washed with 1 N NaOH (2×), water (3×), brine (1×), dried (K$_2$CO$_3$), and concentrated. The residue was purified by RPHPLC, yielding 52 mg (17%) of the title compound as a hydrochloride salt.

$^1$NMR

FD-MS, m/e 417 (m+1)

EXAMPLE 3
Preparation of $N^1$-(4-Clorobenzoyl)-$N^2$-[1-(4-pyridyl)-piperidin-4-ylmethyl]-1,2-benzendiamine

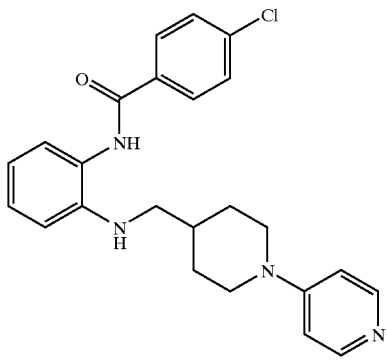

Using a similar procedure to that described in Example 2, Part D, $N^1$-[1-(4-pyridyl)piperidin-4-ylmethyl)-1,2-benzenediamine (167 mg, 0.59 mmol) and 4-chlorobenzoyl chloride (0.075 mL, 0.59 mmol) yielded 137 mg (55%) of the title compound.
$^1$NMR, IR
IS-MS, m/e 419 (p-1)

EXAMPLE 4
Preparation of $N^3$-(4-Methoxybenxoyl)-$N^2$-[1-(4-pyridyl)-piperidin-4-ylmethyl]-2,3-pyridinediamine

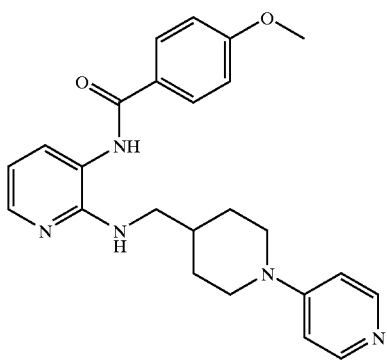

A. 3-nitro-N-[1-(4-pyridyl)piperidin-4-ylmethyl]pyridine-2-amine

A solution of 2-chloro-3-nitropyridine (290 mg, 1.83 mmol), triethylamine (0.26 mL) and 1-(4-pyridyl)-piperidine-4-methylamine (350 mg, 1.83 mmol) in EtOH (10 mL) was heated at reflux. After 17 h, the mixture was concentrated and the residue was purified by chromatography (SiO$_2$, 2 to 4% (2 N NH$_3$ in methanol) in chloroform) yielding 340 mg (60%) of the title compound.
$^1$NMR, IR
IS-MS, m/e 314 (m+1)
Analysis for $C_{25}H_{27}N_3O_3 \cdot CH_3OH$:

| Calcd: | C, 59.12; | H, 6.71; | N, 20.26; |
| Found: | C, 59.00; | H, 6.87; | N, 20.45. |

B. $N^2$-[1-(4-pyridyl)piperidin-4-ylmethyl]-2,3-pyridinediamine

Using a similar procedure to that described in Example 2, Part C, 3-nitro-N-[1-(4-pyridyl)piperidin-4-ylmethyl]pyridine-2-amine (340 mg, 1.09 mmol) and 10% palladium on carbon (200 mg) yielded 300 mg of the title compound, which was used without further purification.
$^1$NMR C. $N^3$-(4-methoxybenzoyl)-$N^2$-[1-(4-pyridyl)piperidin-4-ylmethyl]-2,3-pyridinediamine Using a similar procedure to that described in Example 2, Part D, $N^2$-[1-(4-pyridyl)piperidin-4-ylmethyl]-2,3-pyridinediamine (300 mg, 1.06 mmol) and 4-methoxybenzoyl chloride (200 mg, 1.17 mmol) yielded 67 mg (15%) of the title compound.
$^1$NMR, IR
IS-MS, m/e 418 (m+1)

EXAMPLE 5
Preparation of $N^3$-(4-Chlorobenzoyl)-$N^2$-[1-(4-pyridyl)-piperidin-4-ylmethyl]-2,3-pyridinediamine

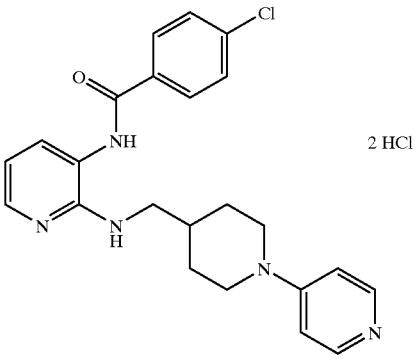

2 HCl

Using a similar procedure to that described in Example 2, Part D, $N^2$-[1-(4-pyridyl)piperidin-4-ylmethyl]-1,2-pyridinediamine (300 mg, 1.06 mmol) and 4-chlorobenzoyl chloride (200 mg, 1.17 mmol) yielded 118 mg (15%) of the title compound as a hydrochloride salt.
$^1$NMR, IR
IS-MS, m/e 422 (m+1)
Analysis for $C_{23}H_{24}ClN_5O \cdot 0.5H_2O \cdot 2HCl$:

| Calcd: | C, 54.83; | H, 5.40; | N, 13.90; |
| Found: | C, 54.90; | H, 5.59; | N, 13.50. |

EXAMPLE 6
Preparation of $N^3$-(3-fluoro-4-methoxybenzoyl)-$N^2$-[1-(4-pyridyl)piperidin-4-ylmethyl)-2,3-pyridinediamine

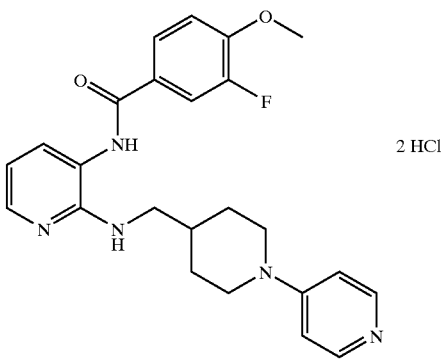

2 HCl

Using a similar procedure to that described in Example 2, Part D, $N^2$-[1-(4-pyridyl)piperidin-4-ylmethyl]-2,3-pyridinediamine (300 mg, 1.06 mmol) and 3-fluoro-4- methoxybenzoyl chloride (200 mg, 1.17 mmol) yielded 118 mg (15%) of the title compound as a hydrochloride salt.
$^1$NMR, IR
IS-MS, m/e 436 (m+1)
Analysis for $C_{24}H_{26}FN_5O_2 \cdot 2HCl$:

| Calcd: | C, 56.70; | H, 5.55; | N, 13.77; |
|---|---|---|---|
| Found: | C, 56.55; | H, 5.46; | N, 13.68. |

EXAMPLE 7
Preparation of $N^3$-(5-Clorothiophen-2-ylcarbonyl)-$N^2$-[1-(4-pyridyl)piperidin-4-ylmethyl]-2,3-pyridinediamine

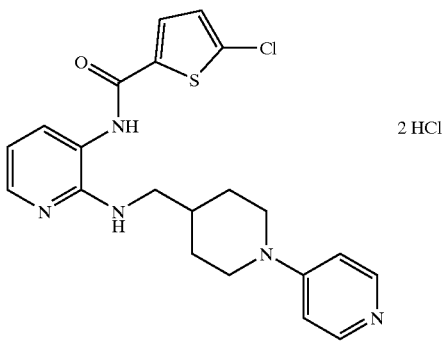

A solution of 5-chlorothiophene-2-carboxylic acid (120 mg, 0.72 mmol) in methylene chloride and DMF (0.005 mL) was treated with oxalyl chloride (0.105 mL, 1.20 mmol). After 0.25 h, the mixture was concentrated and the residue was dissolved in chloroform. This solution was added dropwise to a solution of $N^2$-[1-(4-pyridyl)piperidin-4-ylmethyl]-2,3-pyridinediamine (170 mg, 0.6 mmol) in pyridine and chloroform. The reaction mixture was then purified using a procedure similar to that described in Example 2, Part D, yielding 160 mg (58%) of the title compound as a hydrochloride salt.
$^1$NMR, IR
IS-MS, m/e 428 (m+1)
Analysis for $C_{21}H_{22}ClN_5OS \cdot 2HCl \cdot 0.5H_2O$:

| Calcd: | C, 49.48; | H, 4.94; | N, 13.74; |
|---|---|---|---|
| Found: | C, 49.40; | H, 4.48; | N, 13.30. |

EXAMPLE 8
Preparation of N-(4-Methoxyphenyl)-2-[1-(4-pyridyl)piperidin-4-ylmethyl]aminopyridine-3-carboxamide

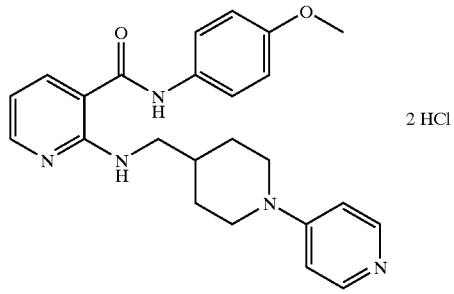

A. 2-chloro-N-(4-methoxyphenyl)pyridine-3-carboxamide
2-Chloronicotinyl chloride hydrochloride (2.94 g, 16.5 mmol) was added in portions to a solution of pyridine (4.0 mL) and 4-anisidine (2.0 g, 16.2 mmol) in chloroform. After 0.5 h, the mixture was poured into EtOAc and 1 N NaOH. The organic layer was washed with 1 N NaOH (1×), water (1×), dried over potassium carbonate, and concentrated. The residue was purified by recrystallization (EtOAc:hexanes) yielding 2.56 g (60%) of the title compound.
$^1$NMR, IR
FD-MS, m/e 262 (m)
Analysis for $C_{13}H_{11}ClN_2O_2$:

| Calcd: | C, 59.44; | H, 4.22; | N, 10.66; |
|---|---|---|---|
| Found: | C, 59.64; | H, 4.45; | N, 10.51. |

B. N-(4-methoxyphenyl)-2-[1-(4-pyridyl)piperidin-4-ylmethyl]aminopyridine-3-carboxamide
A pressure tube (Aldrich) was charged with 2-chloro-N-(4-methoxyphenyl)pyridine-3-carboxamide (139 mg, 0.524 mmol), 1-(4-pyridyl)piperidine-4-methylamine (100 mg, 0.524 mmol), triethylamine (0.22 mL), and ethanol (3 mL). The mixture was placed in a 110° C. bath for 5 days. The mixture was concentrated and the residue purified by RPHPLC, yielding 52 mg (24%) of the title compound as a hydrochloride salt.
$^1$NMR, IR
IS-MS, m/e 418 (m+1)
Analysis for $C_{25}H_{26}N_5O_2 \cdot 2HCl$:

| Calcd: | C, 58.78; | H, 5.96; | N, 14.28; |
|---|---|---|---|
| Found: | C, 58.74; | H, 5.90; | N, 13.91. |

EXAMPLE 9
Preparation of N-(4-Chlorophenyl)-2-[1-(4-pyridyl)piperidin-4-ylmethyl]aminopyridine-3-carboxamide

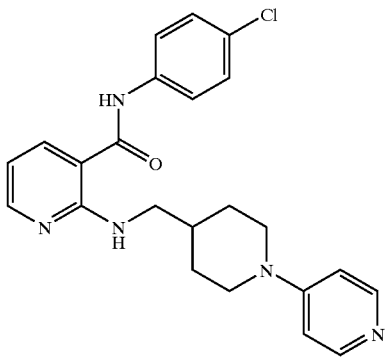

A. 2-chloro-N-(4-chlorophenyl)pyridine-3-carboxamide
Using a similar procedure to that described in Example 8, Part A, 2-chloronicotinyl chloride hydrochloride (500 mg, 2.84 mmol) and 4-chloroaniline (432 mg, 3.41 mmol) yielded 800 mg of the title compound.
$^1$NMR B. N-(4-chlorophenyl)-2-[1-(4-pyridyl)piperidin-4-ylmethyl]aminopyridine-3-carboxamide
Using a similar procedure to that described in Example 8, Part B. 2-chloro-N-(4-chlorophenyl)pyridine-3-carboxamide (125 mg, 0.47 mmol), 1-(4-pyridyl)piperidin-4-ylmethylamine (90 mg, 0.47 mmol), and triethylamine (0.07 mL) yielded 40 mg (24%) of the title compound.
$^1$NMR, IR
IS-MS, m/e 422 (p+)

Analysis for $C_{23}H_{24}ClN_5O$:

| Calcd: | C, 65.47; | H, 5.73; | N, 16.60; |
|---|---|---|---|
| Found: | C, 65.26; | H, 5.77; | N, 16.36. |

EXAMPLE 10
Preparation of $N^3$-(4-Methoxybenzoyl)-$N^4$-[4-(4-pyridyl)-piperidin-4-ylmethyl]-3,4-pyridinediamine

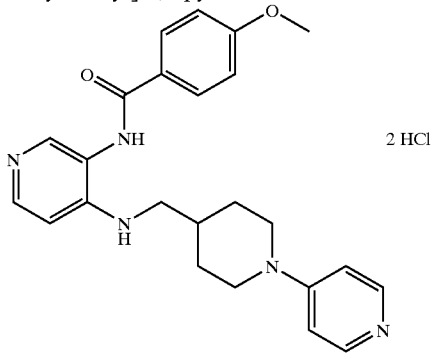

A. 3-nitro-N-[1-(4-pyridyl)piperidin-4-ylmethyl]pyridine-4-amine

Using a similar procedure to that described in Example 4, Part A, 4-methoxy-3-nitropyridine (250 mg, 1.62 mmol), and 1-(4-pyridyl)piperidin-4-ylmethylamine (310 mg, 1.62 mmol) yielded 370 mg (73%) of the title compound.
$^1$NMR B. $N^4$-[1-(4-pyridyl)piperidin-4-ylmethyl]-3,4-pyridinediamine Using a similar procedure to that described in Example 2, Part C, 3-nitro-N-[1-(4-pyridyl)piperidin-4-ylmethyl]pyridine-4-amine (370 mg) yielded 110 mg (40%) of the title compound; which was purified by flash chromatography ($SiO_2$, 5 to 10% (2N $NH_3$ in MeOH) in chloroform).
$^1$NMR C. $N^3$-(4-methoxybenzoyl)-$N^4$-[1-(4-pyridyl)piperidin-4-ylmethyl]-3,4-pyridinediamine Using a similar procedure to that described in Example 2, Part D, $N^4$-[1-(4-pyridyl)piperidin-4-ylmethyl]-3,4-pyridinediamine (110 mg, 0.388 mmol) and 4-methoxybenzoyl chloride (0.66 mL, 0.388 mmol) yielded 10 mg (6%) of the title compound as a hydrochloride salt.
$^1$NMR
IS-MS, m/e 418 (m+1)

EXAMPLE 11
Preparation of N-(4-Chlorophenyl)-3-[1-(4-pyridyl)piperidin-4-ylmethyl]aminopyridine-4-carboxamide

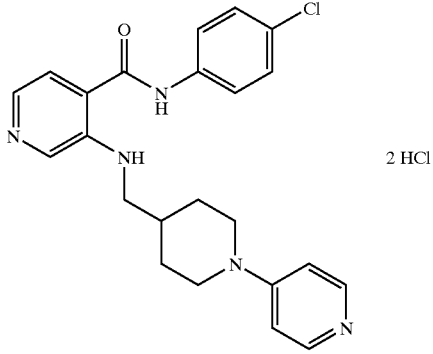

A. 3-Chloro-N-(4-chlorophenyl)pyridine-4-carboxamide

A solution of 3-chloropyridine (1.00 mL, 10.5 mmol) in THF at −78° C. was treated dropwise with a solution of lithium diisopropylamide in THF [freshly prepared by addition of butyllithium (7.21 mL, 11.5 mmol) to diisopropylamine (11.5 mmol)]. After 0.25 h, the mixture was treated with carbon dioxide (g) and slowly warmed to ambient temperature. The mixture was concentrated, partitioned between EtOAc and water, and the aqueous layer was washed with EtOAc (2×). The pH of the aqueous layer was adjusted (~3) by addition of 1 N HCl and then washed with EtOAc (3×). The combined extracts were dried with magnesium sulfate and concentrated. The residue was recrystallized from EtOAc yielding 200 mg (12%) of 3-chloroisonicotinic acid.

A solution of the acid (200 mg) in methylene chloride (6 mL) and dimethyl formamide (0.01 mL) was treated with oxalyl chloride (0.22 mL, 2.55 mmol). After 0.25 h, the mixture was concentrated, the residue dissolved in methylene chloride (6 mL) and then added dropwise to a solution of 4-chloroaniline (323 mg, 2.55 mmol) in pyridine (4 mL). After 1 h, the mixture was concentrated, the residue partitioned between EtOAc and water, the organic layer was washed with 1 N NaOH, brine, and dried with sodium sulfate; then concentrated. The residue was purified by column chromatography ($SiO_2$, 2:3 EtOAc:hexanes) yielding 130 mg (38%) of the title compound.
$^1$NMR
IS-MS, m/e 265 (m−1)

B. N-(4-chlorophenyl)-2-(1-(4-pyridyl)piperidin-4-ylmethyl]aminopyridine-3-carboxamide A mixture of 3-chloro-N-(4-chlorophenyl)pyridine-4-carboxamide (130 mg, 0.49 mmol), 1-(4-pyridyl)piperidine-4-methylamine (187 mg, 0.98 mmol), and copper (1) bromide (70 mg) in dimethylformamide (1 mL) was heated at 110° C. After 18 h, the mixture was diluted with MeON, filtered, and concentrated. The residue was treated with 6:1 chloroform:water (10 mL) followed by MeOH until a homogenoeus solution resulted. The solution was treated with hydrogen sulfide (g), heated at reflux for 0.1 h, and filtered through diatomaceous earth. The filtrate was concentrated and the residue taken up in water, 1 N NaOH, and EtOAc. The aqueous layer was washed with EtOAc (3×), the combined extracts were dried (sodium sulfate), filtered and concentrated. The residue was purified by RPHPLC yielding 29 mg (13%) of the title compound as a hydrochloride salt.
$^1$NMR
IS-MS, m/e 420 (m−1)

EXAMPLE 12
Preparation of N-(6-Indolyl)-2-[1-(4-pyridyl)piperidin-4-ylmethyl]aminopyridine-3-carboxamide

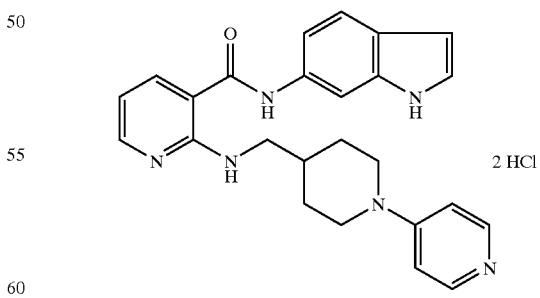

A. Ammonium 2-[1-(4-pyridyl)piperidin-4-ylmethyl]amino-pyridine-3-carboxylate

A mixture of 2-chloronicotinic acid (10.74 g, 67.5 mmol), 1-(4-pyridyl)piperidine-4-methylamine (8.60 g, 45.0 mmol), and potassium carbonate 15.5 g, 112.6 mmol) in dimethylformamide (90 mL) was heated at reflux. After 16 h, the mixture was diluted with methanol, filtered, and concentrated. The residue was dissolved in methanol, acidified with 1 N HCl in ether, heated at reflux for 0.25 h, cooled, and the solid removed by filtration. The filtrate was then treated with 2 M NH$_3$ in methanol until slightly basic, triturated with THF and the resulting solid collected by filtration yielding 10.75 g of the title compound which was used without further purification.

$^1$NMR

IS-MS, m/e 313 (m+1)

B. N-(6-indolyl)-2-[1-(4-pyridyl)piperidin-4-ylmethyl]-aminopyridine-3-carboxamide A solution of ammonium 2-[1-(4-pyridyl)piperidin-4-ylmethyl]aminopyridine-3-carboxylate (3.0 g, 9.12 mmol) in dioxane (45 mL) was treated with phosgene (1.9 M in toluene, 9.50 mL, 18.2 mmol) and the resulting mixture was heated at reflux. After 2 h, the mixture was concentrated yielding the corresponding 4-azaisatoic anhydride which was used without further purification. A solution of the crude anhydride (450 mg, 0.972 mmol) in THF (5 mL) at −78° C. was treated with the magnesium salt of 6-amino-1-tert-butoxy-carbonylindole [3.89 mmol; freshly prepared by addition of methyl magnesium bromide (3.0 M in THF, 1.30 mL, 3.89 mmol) to 6-amino-1-tert-butoxycarbonylindole (900 mg, 3.89 mmol) in THF (10 mL) at −78° C.]. After 17 h, the mixture was treated with a saturated aqueous solution of ammonium chloride, diluted with water, and partitioned between EtOAc. The aqueous layer was washed with EtOAc (3×) and the combined extracts were washed with water (1×), dried with sodium sulfate, and concentrated. The residue was purified by column chromatography (SiO$_2$, 6% (2M NH$_3$ in MeOH) in chloroform) yielding 140 mg (28%) of the coupled product. The coupled product was melted, cooled, and purified by RPHPLC yielding 67 mg (50%) of the title compound.

$^1$NMR, IR

IS-MS, m/e 427 (m+1)

Analysis for C$_{25}$H$_{26}$N$_5$O.HCl.H$_2$O:

| Calcd: | C, 62.43; | H, 6.08; | N, 17.47; |
| Found: | C, 62.25; | H, 5.81; | N, 17.51. |

EXAMPLE 13

Preparation of N-(4-Chlorophenyl)-2-[1-(4-pyridyl)piperidin-4-ylmethyl]aminopyridine-3-methylamine

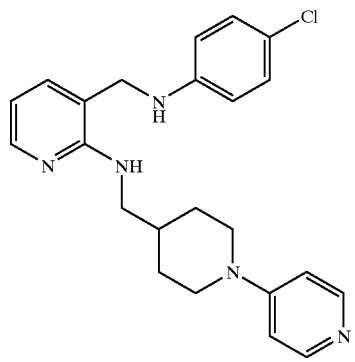

A solution of N-(4-chlorophenyl)-2-[1-(4-pyridyl)piperidin-4-ylmethyl]aminopyridine-3-carboxamide (25 mg, 0.059 mmol) in THF (1 mL) was treated with lithium aluminum hydride (1.0 M in THF, 0.21 mL, 0.21 mmol). The mixture was heated at 65° C. for 4 days, cooled, diluted with methanol (5 m), and loaded onto an SCX ion exchange resin.

The resin was eluted with methanol followed by 2 N NH$_3$ in methanol and fractions containing the desired material were concentrated. The residue was triturated with EtOAc, yielding 15 mg (62%) of the title compound.

$^1$NMR

IS-MS, m/e 409 (m+1)

EXAMPLE 14

Preparation of 5-Chloro-2-(1-isopropylpiperidin-4-ylmethylamino)-N-(2-pyridyl)benzamide

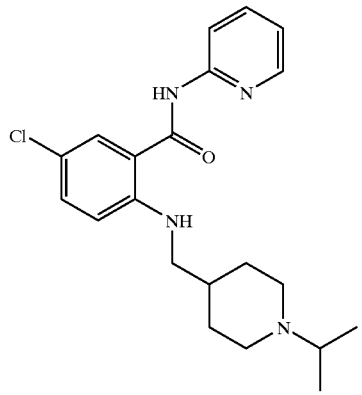

A. 1-Boc-piperidine-4-methanol

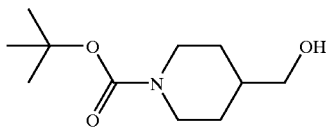

To a solution of Boc-isonipecotic acid (40 g, 0.17 mol) and N-methylmorpholine (19 mL, 0.17 mol) in tetrahydrofuran (900 mL) stirring at −10° C., ethyl chloroformate was slowly added (17 mL, 0.17 mol) via addition funnel. After 30 min, sodium borohydride was added (19.8 g, 0.5 mol) in one portion. The reaction mixture was stirred at −10° C. for 1 h; then it was slowly quenched with methanol. The solvent was removed in vacuo; the resulting residue was diluted with 10% aqueous acetic acid and partitioned between ethyl acetate and water. The aqueous layer was separated and extracted with additional ethyl acetate (2×500 mL). The combined organic extracts were dried with magnesium sulfate, filtered, and concentrated in vacuo to a solid residue which was chromatographed on silica gel. Elution with ethyl acetate-hexanes (1:9 to 1:1) provided the title compound (33.8 g, 90%) as a white solid.

$^1$NMR

B. 1-Boc-piperidine-4-carboxamide

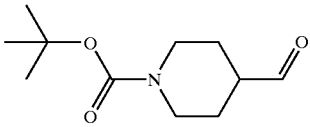

A solution containing oxalyl chloride (8 mL, 87 mmol), in dichloromethane (80 mL) at −78° C. was treated with dimethyl sulfoxide (12 mL, 0.17 mol). After stirring for 15 minutes, 1-Boc-piperidine-4-methanol from above (3.7 g, 17 mmol) was added as a solution in dichloromethane (35 mL) via cannulation. The solution was then stirred at −78° C. for 1 h, after which triethylamine (36 mL, 0.26 mol) was added dropwise to the cold solution. The reaction mixture was allowed to warm to room temperature, upon which a thick white slurry formed. The mixture was poured into a saturated aqueous ammonium chloride solution (200 mL); then the organic layer was separated and the aqueous layer was extracted with dichloromethane (75 mL). The organic layers were combined and washed with brine (75 mL), then dried with magnesium sulfate. The organic phase was filtered and concentrated in vacuo, and the residue was redissolved in a 1:1 mixture of ethyl acetate and hexane and filtered through a Florisil plug (100–200 mesh). The resulting filtrate was concentrated in vacuo to give 3.9 g (100%) of the title aldehyde as a yellow oil, which was used in the next step without further purification.

¹NMR

C. 2-amino-5-chloro-N-(2-pyridyl)benzamide

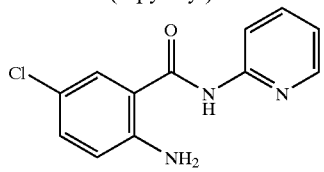

To a solution of 5-chloro-2-nitrobenzoic acid (15 g, 74 mmol) in dichloromethane (300 mL) containing a few drops of N,N-dimethylformamide, oxalyl chloride was slowly added (7.9 mL, 89 mmol). After 2 h at room temperature, the solvent was removed in vacuo and the residue was redissolved in dichloromethane (300 mL). The resulting solution was then treated with pyridine (18 mL, 0.2 mol), followed by 2-aminopyridine (7 g, 74=mol). After 16 h at room temperature, the reaction mixture was concentrated in vacuo to a residue that was partitioned between ethyl acetate and water. The organic phase was separated and washed sequentially with 1 M aqueous citric acid, brine, saturated aqueous sodium bicarbonate, and brine. The organic layer was dried with magnesium sulfate, filtered and concentrated to a small volume. The concentrated solution was then diluted with diethyl ether, which caused the formation of a white precipitate. Sonication followed by filtration provided a white solid (8.6 g, 42%), which was dissolved in ethyl acetate-tetrahydrofuran (1:1) and submitted to hydrogen pressure (4.1 bar) in the presence of catalytic Raney-Nickel (0.8 g) for 16 h at room temperature. The reaction mixture was filtered through diatomaceous earth, and the filtrate was concentrated in vacuo to a solid residue which was purified via silica gel chromatography. Elution with ethyl acetate-hexanes (3:7) provided the title compound as a light-brown solid (4.4 g), which was used directly in the next step without further purification.

¹NMR

FD-MS, m/e 248.0 (m).

D. 2-(1-Boc-piperidin-4-ylmethylidinylimino)-5-chloro-N-(2-pyridyl)benzamide

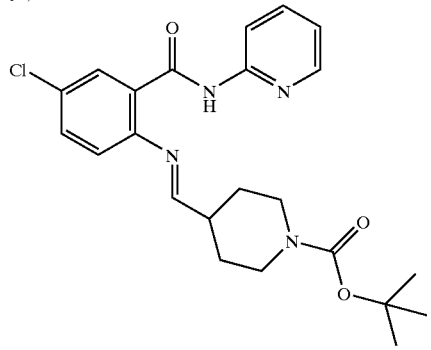

A solution containing 1-Boc-piperidine-4-carboxamide from above (3.7 g, 17 mmol), 2-amino-5-chloro-N-(2-pyridyl)benzamide from above (4.3 g, 17 mmol), and pyridinium p-toluenesulfonate (0.4 g, 1.7 mmol) in benzene (250 mL) was heated at reflux for 24 h with azeotropic removal of water. The mixture was then allowed to cool to room temperature and the solvent was removed in vacuo. The residue was partitioned between ethyl acetate (300 mL) and water (150 mL). The organic phase was separated and washed again with water (150 mL) and then brine (150 mL); then it was dried with magnesium sulfate, filtered and concentrated in vacuo to give 6.2 g (79%) of the desired imine as an orange foam which was used directly in the next step without further purification.

¹NMR

FD-MS, m/e 443.1 (m)

E. 2-(1-Boc-piperidin-4-ylmethylamino)-5-chloro-N-(2-pyridyl)benzamide

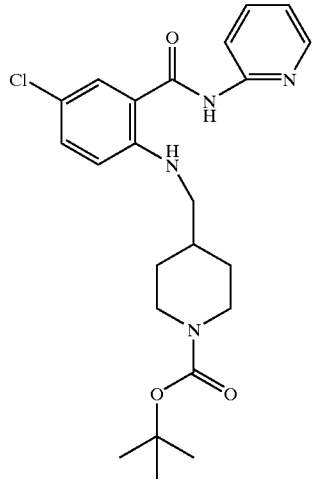

A solution containing 2-(1-Boc-piperidin-4-ylmethylidinylimino)-5-chloro-N-(2-pyridyl)benzamide from above (6.1 g, 14 mmol) and borane-trimethylamine complex (3.0 g, 41 mmol) in glacial acetic acid (100 mL) was heated at 70° C. for 24 h. After cooling to room temperature, the solvent was removed in vacuo; and the residue was partitioned between dichloromethane (200 mL) and water (100 mL). The solution was treated with 2 N sodium hydroxide until neutral; then the organic layer was separated and the aqueous layer was washed again with dichloromethane (100=L). The combined organic extracts were washed with brine (100 m), then dried with magnesium sulfate and filtered. The filtrate was concentrated in vacuo to give 6.23 g (100%) of the title compound as an orange foam, which was used directly in the next step without further purification.

¹NMR

FD-MS, m/e 445.2 (m)

F. 5-chloro-2-(piperidin-4-ylmethylamino)-N-(2-pyridyl)benzamide

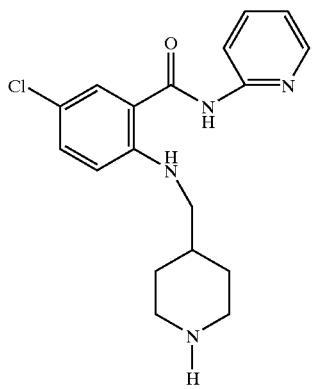

A solution of 2-(1-Boc-piperidin-4-ylmethylamino)-5-chloro-N-(2-pyridyl)benzamide (6.1 g, 14 mmol) in trifluoroacetic acid (125 mL) was stirred at 70° C. for 2 h, then at room temperature for 24 h. The solution was concentrated in vacuo, and the residue was directly applied to a silica gel column. Elution with dichloromethane −2 M ammonia in methanol (9:1) afforded 4.2 g (89%) of the pure title compound as a yellow solid.

$^1$NMR

FD-MS, m/e 345.1 (m)

Analysis for $C_{18}H_{20}ClFN_4O \cdot 0.57CH_2Cl_2$:

| Calcd: | C, 56.71; | H, 5.67; | N, 14.25; |
|---|---|---|---|
| Found: | C, 56.91; | H, 5.61; | N, 13.85. |

G. 5-chloro-2-(1-isopropylpiperidin-4-ylmethylamino)-N-(2-pyridyl)benzamide

A solution of 5-chloro-2-(piperidin-4-ylmethylamino)-N-(2-pyridyl)benzamide from above (1.3 g, 3.7 mmol) in acetone (28 mL) and methanol-acetic acid (95:5) (12 mL) was treated with sodium cyanoborohydride (1.0 g, 15.0 mmol). Gas evolution was observed; the reaction mixture was then stirred at room temperature for 7 h, after which it was concentrated in vacuo to a residue that was purified via silica gel chromatography. Elution with dichloromethane −2 M ammonia in methanol (9:1) provided 0.5 g (34%) of the title compound as a yellow solid.

$^1$NMR mp 118–120° C.

FD-MS, m/e 387.2 (m)

Analysis for $C_{21}H_{27}ClN_4O \cdot 0.25CH_2Cl_2$:

| Calcd: | C, 62.53; | H, 6.79; | N, 13.72; |
|---|---|---|---|
| Found: | C, 62.96; | H, 6.73; | N, 13.92. |

EXAMPLE 15
Preparation of N-(5-Chlorophenyl)-2-(1-isopropylpiperidin-4-ylmethyl)aminopyridine-3-carboxamide

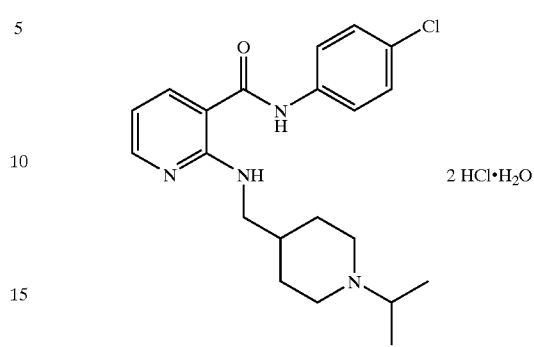

2 HCl·H$_2$O

A. 1-isopropylpiperidine-4-carboxamide

A solution of 200 mL of DMF, containing 50.0 g of isonicotinamide and 60 mL of 2-bromopropane, was refluxed 5.75 h. A white insoluble solid filtered from this cool solution gave 64.9 g (65%) of 1-isopropylpyridinium-4-carboxamide bromide, m/e=165, NMR. Catalytic reduction of this salt, with PtO$_2$ in MeOH, gave 65.2 g (98%) of 1-isopropylpiperidine-4-carboxamide hydrobromide, m/e=171. An aqueous solution of this salt was basified, evaporated to dryness, and extracted with EtOAc to give 39.7 g (90%) of 1-isopropylpiperidine-4-carboxamide free base.

B. 1-isopropylpiperidine-4-methylamine

To a suspension of 10.0 g of LAN in 500 mL of dry THF, at room temperature, was added portionwise 39.7 g of 1-isopropylpiperidine-4-carboxamide and the mixture was refluxed 18 h. The cooled reaction mixture was diluted with 150 mL THF and treated dropwise with 10 mL H$_2$O and 10 mL 5 N NaOH, respectively. The resulting gray mixture was refluxed 18 h, filtered and evaporated. The residue partially dissolved in hexane to give 25.5 g of crude yellow liquid and 6.9 g hexane insoluble starting carboxamide. HPLC purification on silica gel of the 25.5 g liquid, eluting with 20% MeOH-EtOAc gave 1-isopropylpiperidine-4-methylamine (8.5 g, 28%).

$^1$NMR

MS, m/e 157.

C. 2-chloro-N-(4-chlorophenyl)pyridine-3-carboxamide

By methods substantially equivalent to those described in Example 8, Part A, 2-chloro-N-(4-chlorophenyl)pyridine-3-carboxamide was prepared from 2-chloronicotinyl chloride and 4-chloroaniline.

D. N-(5-chlorophenyl)-2-(1-isopropylpiperidin-4-ylmethyl)aminopyridine-3-carboxamide hydrochloride A solution of 0.20 g 2-chloro-N-(4-chlorophenyl)pyridine-3-carboxamide in 5 mL of pyridine was treated with 0.23 g of 1-isopropylpiperidine-4-methylamine and the mixture was refluxed 46.5 h. The cooled mixture was treated with 0.4 mL of 2 N NaOH and evaporated to dryness. The EtOAc extract was purified by radial chromatography (10% MeOH in CHCl$_3$, 1% NH$_4$OH) to give 0.26 g of free base. The HCl salt was isolated as an amorphous foam (0.24 g, 65%).

$^1$NMR

IS-MS, m/e 387 (m+1)

Analysis for $C_{21}H_{27}ClN4O \cdot 2HCl \cdot 1.75H_2O$:

| Calcd: | C, 51.33; | H, 6.67; | N, 11.40; |
|---|---|---|---|
| Found: | C, 50.85; | H, 6.25; | N, 11.22. |

What is claimed is:

1. A compound of formula I,

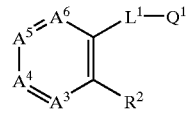

or a pharmaceutically acceptable salt thereof, wherein:

$A^3$, $A^4$, $A^5$ and $A^6$, together with the two carbons to which they are attached, complete a substituted heteroaromatic ring in which one of $A^3$, $A^4$, $A^5$ and $A^6$ is N, and each of the others is $CR^3$, $CR^4$, $CR^5$ or $CR^6$, respectively;

each of $R^3$, $R^4$, $R^5$ and $R^6$ is independently hydrogen or methyl;

$L^1$ is —NH—CO—, —CO—NH— or —CH$_2$—NH— such that —$L^1$—$Q^1$ is —NH—CO—$Q^1$ —CO—NH—$Q^1$ or —CH$_2$—NH—$Q^1$;

$Q^1$ is 2-furanyl, 2-thienyl, 6-indolyl, 6-indolinyl, or 6-indazolyl, in which the 2-furanyl or 2-thienyl may bear a chloro or methyl substituent at the 5-position; 6-indolyl or 6-indazolyl may bear a chloro or methyl substituent at the 3-position; and $R^2$ is —NH—CH$_2$—$Q^2$ in which $Q^2$ is $Q^{2A}$ wherein $Q^{2A}$, showing the —CH$_2$— to which it is attached, is

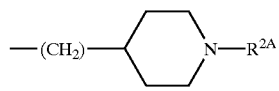

in which $R^{2A}$ is 4-pyridinyl, which is unsubstituted or bears a substituent $R^v$ at the 2- or 3-position, wherein $R^v$ is methyl, hydroxymethyl, cyano, carbamoyl, thiocarbamoyl, or N-hydroxyamidino.

2. The compound as claimed in claim 1 wherein $Q^1$ is 5-chlorothiophen-2-yl, or 6-indolyl.

3. The compound as claimed in claim 1 wherein $R^2$ is [1-(4-pyridinyl)piperin-4-ylmethyl]amino.

4. The compound as claimed in any of claims 1, 2 and 3 wherein $A^3$ is N and each of $A^4$—$A^6$ is CH.

5. The compound as claimed in any of claims 1, 2 and 3 wherein —$L^1$—$Q^1$ is —CO—NH—$Q^1$.

6. The pharmaceutically acceptable salt of a compound of formula I as claimed in claim 1 which is an acid-addition salt made from a basic compound of formula I and an acid which provides a pharmaceutically acceptable anion.

7. A pharmaceutical formulation comprising in association with a pharmaceutically acceptable carrier, diluent or excipient, a novel compound of formula I (or a pharmaceutically acceptable salt thereof) as provided in claim 1.

8. A process for preparing a compound of formula I (or a pharmaceutically acceptable salt thereof) as provided in claim 1 which is selected from (A) for a compound of formula I in which —$L^1$—$Q^1$ is —NH—CO—$Q^1$, acylating an amine of formula II,

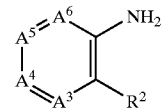

using a corresponding acid of formula HO—CO—$Q^1$, or an activated derivative thereof;

(B) for a compound of formula I in which —$L^1$—$Q^1$ is —CO—NH—$Q^1$, substituting the group $Y^a$ of a compound of formula III

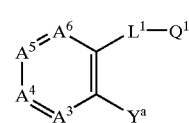

in which $Y^a$ is a conventional leaving group for nucleophilic aromatic substitution with an amine of formula NH$_2$—CH$_2$—$Q^2$;

(C) for a compound of formula I in which —$L^1$—$Q^1$ is —CO—NH—$Q^1$, acylating an amine of formula H$_2$N—$Q^1$, or a deprotonated derivative thereof, using an acid of formula IV, or an activated derivative thereof;

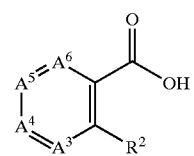

(D) alkylating an amine of formula V

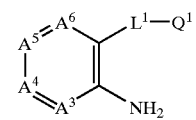

directly, using a compound of formula Y—CH$_2$—$Q^2$, or indirectly by reductive alkylation using an aldehyde of formula $Q^2$—CHO;

(E) for a compound of formula I in which —$L^1$—$Q^1$ is —CH$_2$—NH—$Q^1$, reducing a corresponding compound of formula I in which —$L^1$—$Q^1$ is —CO—NH—$Q^1$;

(H) for a compound of formula I in which $R^{2A}$ is 4-pyridinyl which is unsubstituted or bears a substituent $R^v$ at the 2- or 3-position, substituting the amino nitrogen of a corresponding compound of formula I in which $R^{2A}$ is hydrogen using a corresponding pyridine reagent bearing a leaving group Y at the 4-position;

(J) for a compound of formula I in which $R^{2A}$ is 4-pyridinyl in which $R^v$ is hydroxymethyl, reducing the ester of a corresponding compound of formula I in which $R^v$ is alkoxycarbonyl;

(K) for a compound of formula I in which $R^{2A}$ is 4-pyridinyl in which $R^v$ is carbamoyl, amidating the ester of a corresponding compound of formula I in which $R^v$ is alkoxycarbonyl;

(L) for a compound of formula I in which $R^{2A}$ is 4-pyridinyl in which $R^V$ is thiocarbamoyl, adding $H_2S$ to the nitrile of a corresponding compound of formula I in which $R^V$ is cyano;

(M) for a compound of formula I in which $R^{2A}$ is 4-pyridinyl in which $R^V$ is N-hydroxyamidino, adding $H_2NOH$ to the nitrile of a corresponding compound of formula I in which $R^V$ is cyano;

whereafter, for any of the above procedures, when a functional group is protected using a protecting group, removing the protecting group;

whereafter, for any of the above procedures, when a pharmaceutically acceptable salt of a compound of formula I is required, it is obtained by reacting the basic form of a basic compound of formula I with an acid affording a physiologically acceptable counterion or by any other conventional procedure;

and wherein, unless otherwise specified, $A^3$—$A^6$, $L^1$, $Q^1$ and $R^2$ have any of the values defined in claim 1.

9. A method of inhibiting factor Xa, for the treatment of thromboembolic disorders selected from the group consisting of venous thrombosis, pulmonary embolism, arterial thrombosis, myocardial ischemia, myocardial infraction and cerebral thrombosis, comprising administering to a mammal in need of treatment, a compound of formula I as provided in claim 1.

10. The compound as claimed in claim 4 wherein —$L^1$—$Q^1$ is —CO—NH—$Q^1$.

* * * * *